US012065657B2

(12) United States Patent
Douches et al.

(10) Patent No.: US 12,065,657 B2
(45) Date of Patent: Aug. 20, 2024

(54) OVERCOMING SELF-INCOMPATIBILITY IN DIPLOID PLANTS FOR BREEDING AND PRODUCTION OF HYBRIDS

(71) Applicant: BOARD OF TRUSTEES OF MICHIGAN STATE UNIVERSITY, East Lansing, MI (US)

(72) Inventors: David S. Douches, Okemos, MI (US); Felix E. Enciso-Rodriguez, East Lansing, MI (US); C. Robin Buell, Perry, MI (US); Daniel Zarka, East Lansing, MI (US); Satya Swathi Nadakuduti, Haslett, MI (US); Norma C. Manrique-Carpintero, East Lansing, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 574 days.

(21) Appl. No.: 17/250,407

(22) PCT Filed: Jul. 16, 2019

(86) PCT No.: PCT/US2019/041993
§ 371 (c)(1),
(2) Date: Jan. 18, 2021

(87) PCT Pub. No.: WO2020/018528
PCT Pub. Date: Jan. 23, 2020

(65) Prior Publication Data
US 2022/0025394 A1   Jan. 27, 2022

Related U.S. Application Data

(60) Provisional application No. 62/698,363, filed on Jul. 16, 2018.

(51) Int. Cl.
*C12N 15/82* (2006.01)

(52) U.S. Cl.
CPC ..... *C12N 15/8287* (2013.01); *C12N 15/8213* (2013.01)

(58) Field of Classification Search
None
See application file for complete search history.

(56) References Cited

U.S. PATENT DOCUMENTS

| 5,585,543 A | 12/1996 | Kao |
| 2006/0123514 A1 | 6/2006 | Janssens et al. |
| 2021/0054391 A1* | 2/2021 | Huang ............ A01H 6/827 |

FOREIGN PATENT DOCUMENTS

| RU | 2505957 | * | 2/2014 |

OTHER PUBLICATIONS

GenBank Accession No. L36464.1 entitled "Solanum chacoense S11 gene, complete cds" dated Oct. 4, 1994 (2 pages) (Year: 1994).*

(Continued)

*Primary Examiner* — Matthew R Keogh
*Assistant Examiner* — Rebecca Stephens
(74) *Attorney, Agent, or Firm* — McKee, Voorhees & Sease, PLC

(57) ABSTRACT

The present invention relates to methods for controlling hybridization in plants and producing hybrid plants. The present invention also relates to nucleic acids encoding amino acid sequences for self-incompatibility (SI) proteins in plants, and the use thereof for the manipulation of SI, including seed production, in plants, particularly of the Solanaceae family. The present invention also relates to kits, compositions, constructs and vectors including such nucleic acids, and related polypeptides, regulatory elements and (Continued)

methods as well as resultant plant varieties developed through the use of self-pollination.

11 Claims, 16 Drawing Sheets

Specification includes a Sequence Listing.

(56) References Cited

OTHER PUBLICATIONS

The SAES-422 Multistate Research Activity Accomplishments Report dated Jun. 13, 2017, 7 total pages (summarizing the discussion had during an annual meeting that took place Dec. 5, 2016 and Dec. 6, 2016). (Year: 2017).*

Matton et al. "Hypervariable Domains of Self-Incompatibility RNases Mediate Allele-Specific Pollen Recognition" (1997 Plant Cell 9:1757-1766). (Year: 1997).*

Zsogon et al. ("Genome editing as a tool to achieve the crop ideotype and de novo domestication of wild relatives: Case study in tomato" 2017 Plant Science 256:120-130) (Year: 2017).*

Butler et al. ("Generation and Inheritance of Targeted Mutations in Potato (*Solanum tuberosum* L.) Using the CRISPR/Cas System" 2015 PLoS One 10(12):e0144591 (12 total pages) doi: 10.1371/journal.pone.0144591). (Year: 2015).*

Zsogon et al. ("Genome editing as a tool to achieve the crop ideotype and de novo domestication of wild relatives: Case study in tomato" 2017 Plant Science 256:120-130; of record nonfinal action dated Aug. 1, 2023) (Year: 2017).*

Enciso-Rodriguez et al., "Overcoming self-incompatibility in diploid potato using CRISPR-Cas9", Powerpoint, 9 pages, North Central Meeting in Chicago, IL, Dec. 10, 2018.

Enciso-Rodriguez et al., "Breaking self-incompatibility in diploid potato using genome editing",Powerpoint, 17 pages, PAA meeting in Boise, ID, Jul. 24, 2018.

Enciso-Rodriguez et al., "Breaking self-incompatibility in diploid potato using genome editing", Handout, 3 pages, PAG XXVI meeting in San Diego, CA, Jan. 16, 2018.

Enciso-Rodriguez et al., "Overcoming self-incompatibility in diploid potato using genome editing" Michigan State University, Poster, 1 page, Aug. 23, 2018.

Jansky et al., "Reinventing Potato as a Diploid Inbred Line-Based Crop", Crop Science, vol. 56, pp. 1412-1422, Jul. 7, 2016.

* cited by examiner

| Line | Transform. events | S-RNAse knockouts |
|---|---|---|
| DRH195 | 164 | 20 |
| DRH-310 | 84 | 4 |
| MSX91410 | 9 | 1 |

FIG. 4B

```
            gRNA1                                                                    gRNA2
WT       GATTTCGACAAATTGCAACTGGTATTAACATGGCCACCATCAT //  481 bp  // CAGATGGATCCTGATATCAAGTGTACTGAAGCAGCACCGGAA    0
195-104.1 GATTTCGACAAATTGCAACTGGTATTAACATGGCCACCATCAT // NNNNNNNNNNNNNNNNNNNNNNNNNNNNN // NNNNNNNNNNNNNNNNNNNNNNNNNNNNNNNNNNCTGAAGGAGCACCGGAA inv.524,+20
195-104.2 GATTTCGACAAATTGCAACTGGT--------------------- //        // CAGATGGATCCTGATATCAAGTGT------GAAGGAGCACCGGAA -527
195-105.1 GATTTCGACAAATTGCAACTGGTA-------------CATGGCCACCATCAT //   // CAGATGGATCCTGATATCAAGTGT------GAAGGAGCACCGGAA -4,-3
195-105.2 GATTTCGACAAATTGCAACTGGT--------------------- //        // CAGATGGATCCTGATATCAAGTGTACTGAAGGAGCACCGGAA -527
195-137.1 GATTTC-------------------------------------- //        // -----------------------------------------  -73
195-137.2 GATTTCGACAAATTGCAACTGGTATT------------------ //        // ------------------------------CTGAAGGAGCACCGGAA -555,+4
310-8    GATTTCGACAAATTGCAACTGGTATT------------------ //        // ------------------------------           -523
310-33   GATTTCGACAAATTGCAACTGGTATT------------------ //        // ------------------------------           -128
310-47   GATTTC-------------------------------------- //        // ------------------------------CTGAAGGAGCACCGGAA -544,+4
```

| Line | Num. Explants | T₀ lines | Transformation Efficiency (%)‡ | Mutant deletion polymorphism type | |
|---|---|---|---|---|---|
| | | | | Single§ | Double |
| DRH-195 | 186 | 162 | 98 | | 7 |
| DRH-310 | 276 | 78 | 93 | 3 | |

‡ Calculated as the percentage of T₀ lines with Cas9 integration

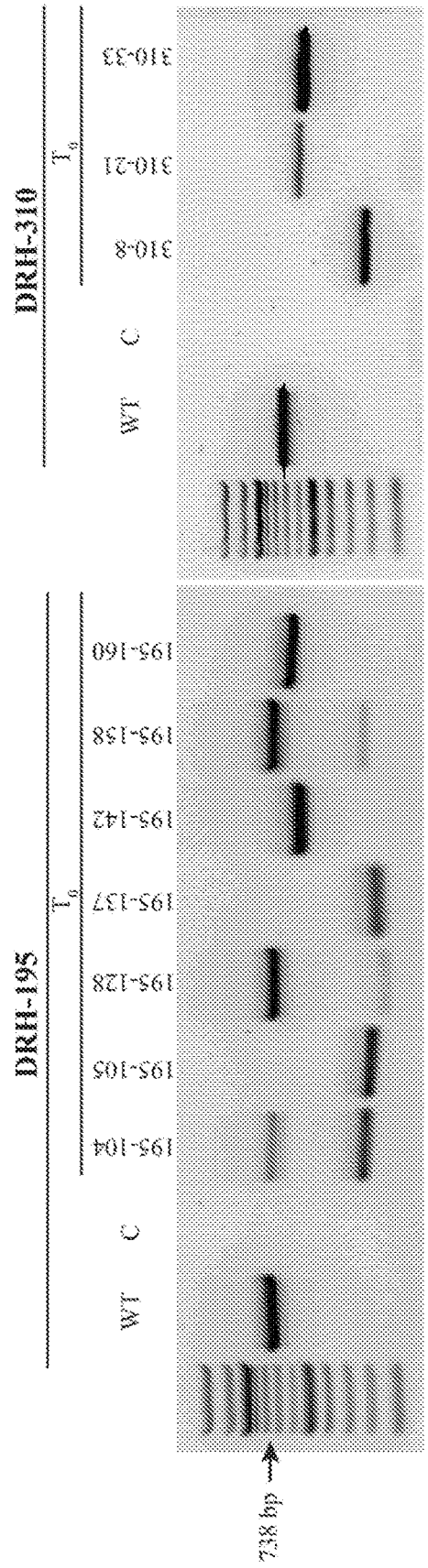

SEQUENCE LISTING

```
<160> NUMBER OF SEQ ID NOS: 54

<210> SEQ ID NO 1
<211> LENGTH: 738
<212> TYPE: DNA
<213> ORGANISM: Unknown
<220> FEATURE:
<223> OTHER INFORMATION: Solanaceae

<400> SEQUENCE: 1
atgtttaaat cactgcttac atcgactctc ttcattgtgc ttttttctct ctcttctact      60
tatggggatt tcgacaaatt gcaactggta ttaacatggc caccatcatt ttgccacgcc     120
aataattgtc aacgaatagt tccaaaaaac tttacgattc acggtctttg gccggataag    180
gagggaccac agctgttgaa gtactgcaag ccaaaactta cctataacta tttcagtgta     240
agcagcttta ttattttctt cagaaccgga tccttttctg ttttgtttaa tttactgaaa      300
agcttatttt ttaatttctt gcaggataag atgctcaatg atcttgacaa acactggatt     360
cagttgaaga ttgatcaagc ttctgctcga aaggaccaac cagcatggaa atatcaatat    420
ctaaagcacg atcctgctg tcagaaaatc tacaatcaaa acacgtattt tagtttagcc     480
ttgcgcttaa aagataggtt tgatcttctg agaactctcc aaatacatag aattgttcct    540
ggatcaagtt atacatttga agaaatcttt gacgccgtca aaacagttac tcagatggat   600
cctgatatca agtgtactga aggagcaccg gaactatatg agataggcat atgttttacc    660
ccaaatggag atagtctagt tcgttgtcgt caaagtgaaa catgcgacaa aacagggaaa    720 atattttcc gtccctga                                                    738

<210> SEQ ID NO 2
<211> LENGTH: 738
<212> TYPE: DNA
<213> ORGANISM: Unknown
<220> FEATURE:
<223> OTHER INFORMATION: Solanaceae

<400> SEQUENCE: 2
atgtttaaat cactgcttac atcaactctc ttcattgtgc ttttttatct ctcttctact      60
```

| tatgcggatt tcgacaaatt gcaactggta ttaacatggc caccatcatt ttgccacgcc | 120 |
| aatagttgtc aacgaatagt tccaaaaaat tttacgattc acggtctttg gccggataag | 180 |
| gagggaccac agctgttgaa gtactgcaag ccaaaactta aatataaata tttcagtgta | 240 |
| aacagcttta ttattttctt cagaaccgga tccttttcta ttctgtttaa tttagtgaaa | 300 |
| cgattgtttt tgaatttctt gcaggataag atgttcaacg atcttgacaa acactggatt | 360 |
| cagttgaagt ttgatgaaga ttctgctcta aaagaccaac gagcatgaa atatcaatat | 420 |
| ttaaagcatg gatcttgttg tcagaaaatg tacaaccaaa acacgtattt tagtctagcc | 480 |
| ttgcgcttaa aagacaggtt tgatcttctg agaactctcc aaatacatca tattttcct | 540 |
| ggatcaagtt atacatttga agaaatcgtt gacgccgtca aacagttac tcagatggat | 600 |
| cctgatatca gtgtactga aggagcaccg gaactatatg agataggcat atgttttacc | 660 |
| ccaaatggag atagtctagt tggttgtcgt caaagtgaaa catgcgacaa aacagggaaa | 720 |
| atattttcc gtccctga | 738 |

<210> SEQ ID NO 3
<211> LENGTH: 738
<212> TYPE: DNA
<213> ORGANISM: Unknown
<220> FEATURE:
<223> OTHER INFORMATION: Solanaceae

<400> SEQUENCE: 3

| atgtttaaat cactgcttac atcaactctc ttcattgtgc ttttttctct ctcttctact | 60 |
| tatgcggatt tcgacaaatt gcaactggta ttaacatggc caccatcatt ttgccacgcc | 120 |
| aatagttgtc aacgaatagt tccaaaaaat tttacgattc acggtctttg gccggataag | 180 |
| gagggaccac agctgttgaa gtactgcaag ccaaaactta aatataacta tttcagtgta | 240 |
| aacagcttta ttattttctt cagaaccgga tccttttcta ttctgtttaa tttagtgaaa | 300 |
| cgattgtttt tgaatttctt gcaggataag atgctcaatg accttgacaa acactggatt | 360 |
| cagttgaagg ttgatcaagc ttctgctcta aaagaccaac gagcatgaa atatcaatat | 420 |
| ctaaagcatg gatcctgctg tcagaaaatc tataatcaaa acacgtattt tagtttagcc | 480 |
| ttgcacttaa aagataggtt tgatcttctg agaactctcc aaatacatag aattgttcct | 540 |
| ggatcaagct atacatttga agaaatcgtt gacgccgtca aacagttac tcagatggat | 600 |
| cctgatatca gtgtactga aggagcaccg gaactatatg agataggcat atgttttacc | 660 |
| ccaaatggag atagtctagt tggttgtcgt caaagtgaaa catgcgacaa aacagggaaa | 720 |
| atattttcc gtccctga | 738 |

<210> SEQ ID NO 4
<211> LENGTH: 737
<212> TYPE: DNA
<213> ORGANISM: Unknown
<220> FEATURE:
<223> OTHER INFORMATION: Solanaceae

<400> SEQUENCE: 4

| atgtttaatc actgcttaca tcractctct tcattgtgct tttttctctc tcttctactt | 60 |
| atgsggattt cgacaaattg caactggtat taacatggcc accatcattt tgccacgcca | 120 |
| atarttgtca acgaatagtt ccaaaaaayt ttacgattca cggtctttgg ccggataagg | 180 |
| agggaccaca gctgttgaag tactgcaagc caaaacttam mtataactat ttcagtgtaa | 240 |

```
rcagctttat tatttctc agaaccggat cctttctrt tytgtttaat ttastgaaam    300
gmttrttttt kaatttcttg caggataaga tgctcaatga ycttgacaaa cactggattc    360
agttgaagrt tgatcaagct tctgctckaa argaccaacs agcatggaaa tatcaatatc    420
taaagcaygg atcctgctgt cagaaaatct ayaatcaaaa cacgtattt agtttagcct    480 tgcrcttaaa agataggttt gatcttctga gaactctcca aatacataga attgttcctg    540
gatcaagyta tacatttgaa gaaatckttg acgccgtcaa aacagttact cagatggatc    600
ctgatatcaa gtgtactgaa ggagcaccgg aactatatga gataggcata tgttttaccc    660
caaatggaga tagtctagtt sgttgtcgtc aaagtgaaac atgcgacaaa acagggaaaa    720 tattttccg tccctga    737
```

```
<210> SEQ ID NO 5
<211> LENGTH: 344
<212> TYPE: DNA
<213> ORGANISM: Unknown
<220> FEATURE:
<223> OTHER INFORMATION: Solanaceae

<400> SEQUENCE: 5
atgtttaaat cactgcttac atcaatatct aaagcatgga tcctgctgtc agaaaatcta    60
taatcaaaac acgtattta gtttagcctt gcacttaaaa gataggtttg atcttctgag    120
aactctccaa atacatagaa ttgttcctgg atcaagctat acatttgaag aaatcgttga    180
cgccgtcaaa acagttactc agatggatcc tgatatcaag tactgaagga gcaccggaac    240
tatatgagat aggcatatgt ttacccaa atggagatag tctagttcgt tgtcgtcaaa    300
gtgaaacatg cgacaaaaca gggaaaatat ttttccgtcc ctga    344
```

```
<210> SEQ ID NO 6
<211> LENGTH: 599
<212> TYPE: DNA
<213> ORGANISM: Unknown
<220> FEATURE:
<223> OTHER INFORMATION: Solanaceae

<400> SEQUENCE: 6
atgtttaaat cactgcttac atcgactctc ttcattgtgc ttttttctct ctcttctact    60 tatgggatt tcgacaaatt gcaacatggc caccatcatt ttgccacgcc aataattgtc    120
aacgaatagt tccaaaaac tttacgattc acggtctttg gccggataag gagggaccac    180
agctgttgaa gtactgcaag ccaaaactta cctataacta tttcagtgta agcagcttta    240 ttatttctt cagaaccgga tcctttctg ttttgtttaa tttactgaaa agcttatttt    300
ttaatttctt gcaggataag atgctcaatg atcttgacaa acactggatt cagttgaaga    360
ttgatcaagc ttctgctcga aaggaccaac cagcatggaa atatcaatat ctaaagcacg    420
gatcctgctg tcagaaaatc tacaatcaaa acacgtattt tagtttagcc ttgcgcttaa    480
aagataggtt tgatcttctg agaactctcc aaatacatag aattgttcct ggatcaagtt    540
atacatttga agaaatcttt gacgccgtca aaacagggaa atatttttc cgtccctga    599
```

```
<210> SEQ ID NO 7
<211> LENGTH: 664
<212> TYPE: DNA
<213> ORGANISM: Unknown
<220> FEATURE:
<223> OTHER INFORMATION: Solanaceae

<400> SEQUENCE: 7
```

```
atgtttaaat cactgcttac atcgactctc ttcattttgc cacgccaata attgtcaacg    60
aatagttcca aaaaacttta cgattcacgg tctttggccg gataaggagg gaccacagct   120
gttgaagtac tgcaagccaa aacttaccta taactatttc agtgtaagca gctttattat   180
tttcttcaga accggatcct tttctgtttt gtttaattta ctgaaaagct tatttttaa    240
tttcttgcag gataagatgc tcaatgatct tgacaaacac tggattcagt tgaagattga   300
tcaagcttct gctcgaaagg accaaccagc atggaaatat caatatctaa agcacggatc   360
ctgctgtcag aaaatctaca atcaaaacac gtattttagt ttagccttgc gcttaaaaga   420
taggtttgat cttctgagaa ctctccaaat acatagaatt gttcctggat caagttatac   480
atttgaagaa atctttgacg ccgtcaaaac agttactcag atggatcctg atatcaagtg   540
tactgaagga gcaccggaac tatatgagat aggcatatgt tttaccccaa atggagatag   600
tctagttcgt tgtcgtcaaa gtgaaacatg cgacaaaaca gggaaaatat ttttccgtcc   660
ctga                                                               664
```

<210> SEQ ID NO 8
<211> LENGTH: 214
<212> TYPE: DNA
<213> ORGANISM: Unknown
<220> FEATURE:
<223> OTHER INFORMATION: Solanaceae

<400> SEQUENCE: 8

```
atgtttaaat cactgcttac atcgactctc ttcattgtgc ttttttctct ctcttctact    60
tatggggatt tcgacaaatt gcaactggta ttctgaagga gcaccggaac tatatgagat   120
aggcatatgt tttaccccaa atggagatag tctagttcgt tgtcgtcaaa gtgaaacatg   180
cgacaaaaca gggaaaatat ttttccgtcc ctga                               214
```

<210> SEQ ID NO 9
<211> LENGTH: 178
<212> TYPE: DNA
<213> ORGANISM: Unknown
<220> FEATURE:
<223> OTHER INFORMATION: Solanaceae

<400> SEQUENCE: 9

```
atgtttaaat cactgcttac atcaactctc ttcattgtgc ttttttctct ctcttctact    60
tatgcggatt tctacttatg agataggcat atgttttacc ccaaatggag atagtctagt   120
tggttgtcgt caaagtgaaa catgcgacaa acagggaaa atattttttcc gtccctga    178
```

<210> SEQ ID NO 10
<211> LENGTH: 210
<212> TYPE: DNA
<213> ORGANISM: Unknown
<220> FEATURE:
<223> OTHER INFORMATION: Solanaceae

<400> SEQUENCE: 10

```
atgtttaaat cactgcttac atcgactctc ttcattgtgc ttttttctct ctcttctact    60
tatggggatt tcgacaaatt gcaactggct gaaggagcac cggaactata tgagataggc   120
atatgtttta ccccaaatgg agatagtcta gttcgttgtc gtcaaagtga acatgcgac   180
aaaacaggga aatatttttt ccgtccctga                                   210
```

<210> SEQ ID NO 11

```
<211> LENGTH: 214
<212> TYPE: DNA
<213> ORGANISM: Unknown
<220> FEATURE:
<223> OTHER INFORMATION: Solanaceae

<400> SEQUENCE: 11
atgtttaaat cactgcttac atcaactctc ttcattgtgc ttttttctct ctcttctact      60
tatgcggatt tcgacaaatt gcaactggta ttctgaagga gcaccggaac tatatgagat     120
aggcatatgt tttaccccaa atggagatag tctagttggt tgtcgtcaaa gtgaaacatg     180
cgacaaaaca gggaaaatat ttttccgtcc ctga                                 214

<210> SEQ ID NO 12
<211> LENGTH: 214
<212> TYPE: DNA
<213> ORGANISM: Unknown
<220> FEATURE:
<223> OTHER INFORMATION: Solanaceae

<400> SEQUENCE: 12
atgtttaaat cactgcttac atcaactctc ttcattgtgc ttttttctct ctcttctact      60
tatggggatt tcgacaaatt gcaactggta ttactgaagg agcaccggaa ctatatgaga     120
taggcatatg ttttacccca atggaatag tctagttcgt tgtcgtcaaa gtgaaacatg      180
cgacaaaaca gggaaaatat ttttccgtcc ctga                                 214

<210> SEQ ID NO 13
<211> LENGTH: 609
<212> TYPE: DNA
<213> ORGANISM: Unknown
<220> FEATURE:
<223> OTHER INFORMATION: Solanaceae

<400> SEQUENCE: 13
atgtttaaat cactgcttac atcaactctc ttcattgtgc ttttttctct ctcttctact      60
tatgcggatt tcgacaaatt gcaactggta ttttacgatt cacggtcttt ggccggataa     120
ggagggacca cagctgttga agtactgcaa gccaaaactt aaatataact atttcagtgt     180
aaacagcttt attattttct tcagaaccgg atccttttct attctgttta atttagtgaa     240
acgattgttt tgaatttct tgcaggataa gatgctcaat gacctgaca aacactggat       300 tcagttgaag gttgatcaag cttctgctct aaaagaccaa cgagcatgga aatatcaata     360
tctaaagcat ggatcctgct gtcagaaaat ctataatcaa acacgtatt ttagtttagc      420 cttgcactta aaagataggt tgatcttct gagaactctc caaatacata gaattgttcc      480
tggatcaagc tatacatttg aagaaatcgt tgacgccgtc aaaacagtta cccaaatgga     540
gatagtctag ttggttgtcg tcaaagtgaa acatgcgaca aaacagggaa atatttttc     600 cgtccctga                                                             609

<210> SEQ ID NO 14
<211> LENGTH: 609
<212> TYPE: DNA
<213> ORGANISM: Unknown
<220> FEATURE:
<223> OTHER INFORMATION: Solanaceae

<400> SEQUENCE: 14
atgtttaaat cactgcttac atcaactctc ttcattgtgc ttttttctct ctcttctact      60
tatgcggatt tcgacaaatt gcaactggta ttttacgatt cacggtcttt ggccggataa     120
```

```
ggagggacca cagctgttga agtactgcaa gccaaaactt aaatataact atttcagtgt    180
aaacagcttt attattttct tcagaaccgg atccttttct attctgttta atttagtgaa    240
acgattgttt ttgaatttct tgcaggataa gatgctcaat gaccttgaca aacactggat    300
tcagttgaag gttgatcaag cttctgctct aaaagaccaa cgagcatgga aatatcaata    360
tctaaagcat ggatcctgct gtcagaaaat ctataatcaa aacacgtatt ttagtttagc    420
cttgcactta aaagataggt ttgatcttct gagaactctc caaatacata gaattgttcc    480
tggatcaagc tatacatttg aagaaatcgt tgacgccgtc aaaacagtta cccaaatgga    540
gatagtctag ttggttgtcg tcaaagtgaa acatgcgaca aaacagggaa atatttttc    600 cgtccctga                                                           609
```

<210> SEQ ID NO 15
<211> LENGTH: 211
<212> TYPE: DNA
<213> ORGANISM: Unknown
<220> FEATURE:
<223> OTHER INFORMATION: Solanaceae

<400> SEQUENCE: 15

```
atgtttaaat cactgcttac atcaactctc ttcattgtgc ttttttctct ctcttctact     60
tatgcggatt tcgacaaatt gcaactggtc tgaaggagca ccggaactat atgagatagg    120
catatgtttt accccaaatg gagatagtct agttggttgt cgtcaaagtg aaacatgcga    180
caaaacaggg aaaatatttt tccgtccctg a                                  211
```

<210> SEQ ID NO 16
<211> LENGTH: 609
<212> TYPE: DNA
<213> ORGANISM: Unknown
<220> FEATURE:
<223> OTHER INFORMATION: Solanaceae

<400> SEQUENCE: 16

```
atgtttaaat cactgcttac atcaactctc ttcattgtgc ttttttctct ctcttctact     60
tatgcggatt tcgacaaatt gcaactggta ttttacgatt cacggtcttt ggccggataa    120
ggagggacca cagctgttga agtactgcaa gccaaaactt aaatataact atttcagtgt    180
aaacagcttt attattttct tcagaaccgg atccttttct attctgttta atttagtgaa    240
acgattgttt ttgaatttct tgcaggataa gatgctcaat gaccttgaca aacactggat    300
tcagttgaag gttgatcaag cttctgctct aaaagaccaa cgagcatgga aatatcaata    360
tctaaagcat ggatcctgct gtcagaaaat ctataatcaa aacacgtatt ttagtttagc    420
cttgcactta aaagataggt ttgatcttct gagaactctc caaatacata gaattgttcc    480
tggatcaagc tatacatttg aagaaatcgt tgacgccgtc aaaacagtta cccaaatgga    540
gatagtctag ttggttgtcg tcaaagtgaa acatgcgaca aaacagggaa atatttttc    600 cgtccctga                                                           609
```

<210> SEQ ID NO 17
<211> LENGTH: 627
<212> TYPE: DNA
<213> ORGANISM: Unknown
<220> FEATURE:
<223> OTHER INFORMATION: Solanaceae

<400> SEQUENCE: 17

```
atgtttaaat cactgcttac atcaactctc ttcattgtgc ttttttctct ctcttctact    60
tatgcggatt tcgacaaatt gcaactggta ttaaacatgg ccaccatcat tttgccacgc   120
caatagttgt caacgaatag ttccaaaaaa ttttacgatt cacggtcttt ggccggataa   180
ggagggacca cagctgttga agtactgcaa gccaaaactt aaatataact atttcagtgt   240
aaacagcttt attattttct tcagaaccgg atccttttct attctgttta atttagtgaa   300
acgattgttt ttgaatttct tgcaggataa gatgctcaat gaccttgaca aacactggat   360
tcagttgaag gttgatcaag cttctgctct aaaagaccaa cgagcatgga aatatcaata   420
tctaaagcat ggatcctgct gtcagaaaat ctataatcaa acacgtatt  ttagtttagc   480 cttgcactta aaagataggt tgatcttct  gagaactctc caaatacata gaattgttcc   540
tggataataa ctcacacttg ccactgcttc atctatcgtc aaagtgaaac atgcgacaaa   600
acagggaaaa tattttccg  tccctga                                       627

<210> SEQ ID NO 18
<211> LENGTH: 215
<212> TYPE: DNA
<213> ORGANISM: Unknown
<220> FEATURE:
<223> OTHER INFORMATION: Solanaceae

<400> SEQUENCE: 18
atgtttaaat cactgcttac atcaactctc ttcattgtgc ttttttctct ctcttctact    60
tatgcggatt tcgacaaatt gcaactggta ttactgaagg agcaccggaa ctatatgaga   120
taggcatatg ttttaccccca aatggagata gtctagttgg ttgtcgtcaa agtgaaacat   180
gcgacaaaac agggaaaata ttttccgtc cctga                               215

<210> SEQ ID NO 19
<211> LENGTH: 621
<212> TYPE: DNA
<213> ORGANISM: Unknown
<220> FEATURE:
<223> OTHER INFORMATION: Solanaceae

<400> SEQUENCE: 19
atgtttaaat cactgcttac atcaactctc ttcattgtgc ttttttctct ctcttctact    60
tatgcggatt tcgacaaatt gcaactggcc accatcattt tgccacgcca atagttgtca   120
acgaatagtt ccaaaaaatt ttacgattca cggtctttgg ccggataagg agggaccaca   180
gctgttgaag tactgcaagc caaaacttaa atataactat ttcagtgtaa acagctttat   240
tattttcttc agaaccggat ccttttctat tctgtttaat ttagtgaaac gattgttttt   300
gaatttcttg caggataaga tgctcaatga ccttgacaaa cactggattc agttgaaggt   360
tgatcaagct tctgctctaa aagaccaacg agcatggaaa tatcaatatc taaagcatgg   420
atcctgctgt cagaaaatct ataatcaaaa cacgtatttt agtttagcct tgcacttaaa   480
agataggttt gatcttctga gaactctcca aatacataga attgttcctg aacatcacca   540
agcacctttg agatagtct  agttggttgt cgtcaaagtg aaacatgcga caaacaggg   600 aaaatatttt tccgtccctg a                                             621

<210> SEQ ID NO 20
<211> LENGTH: 351
<212> TYPE: DNA
<213> ORGANISM: Unknown
<220> FEATURE:
<223> OTHER INFORMATION: Solanaceae
```

<400> SEQUENCE: 20

```
atgtttaaat cactgcttac atcaactctc ttcattgtgc ttttttctct ctcttctact      60
tatgcggatt tcgacaaatt gcaactggta ttacccatgg ccaccatcat tttgccacgc     120
caatagttgt caacgaatag ttccaaaaaa ttttacgatt cacggtcttt ggccggataa     180
ggagggacca cagctgttga agtactgcaa gccaaaactt aaatataact atttcagcgt     240
aaacagcttt attattttct tcagaaccgg atccttttct attctgttta atttagtgaa     300
aaaattgcta tagaatctat tgaaatgttt atctgcaatg actatgaatg c             351
```

<210> SEQ ID NO 21
<211> LENGTH: 595
<212> TYPE: DNA
<213> ORGANISM: Unknown
<220> FEATURE:
<223> OTHER INFORMATION: Solanaceae

<400> SEQUENCE: 21

```
atgtttaaat cactgcttac atcaactctc ttcattgtgc ttttttctct ctcttctact      60
tatgcggatt tcgacaaatt gcaactggac atggccacca tcattttgcc acgccaatag    120
ttgtcaacga atagttccaa aaattttac gattcacggt ctttggccgg ataaggaggg     180
accacagctg ttgaagtact gcaagccaaa acttaaatat aactatttca gtgtaaacag    240
ctttattatt ttcttcagaa ccggatcctt ttctattctg tttaatttag tgaaacgatt    300
gtttttgaat tcttgcagg ataagatgct caatgacctt gacaaacact ggattcagtt     360
gaaggttgat caagcttctg ctctaaaaga ccaacgagca tggaaatatc aatatctaaa    420
gcatggatcc tgctgtcaga aaatctataa tcaaaacacg tatttagtt tagccttgca     480
cttaaaagat aggtttgatc ttctgagaac tctccaaata catagaattg ttcctggatc    540
aagctataca tttgaaacat gcgacaaaac agggaaaata ttttccgtc cctga          595
```

<210> SEQ ID NO 22
<211> LENGTH: 20
<212> TYPE: DNA
<213> ORGANISM: Unknown
<220> FEATURE:
<223> OTHER INFORMATION: Solanaceae

<400> SEQUENCE: 22

```
aattgcaact ggtattaaca                                                  20
```

<210> SEQ ID NO 23
<211> LENGTH: 20
<212> TYPE: DNA
<213> ORGANISM: Unknown
<220> FEATURE:
<223> OTHER INFORMATION: Solanaceae

<400> SEQUENCE: 23

```
ggtctttggc cggataagga                                                  20
```

<210> SEQ ID NO 24
<211> LENGTH: 20
<212> TYPE: DNA
<213> ORGANISM: Unknown
<220> FEATURE:
<223> OTHER INFORMATION: Solanaceae

<400> SEQUENCE: 24

```
cctgatatca agtgtactga                                              20

<210> SEQ ID NO 25
<211> LENGTH: 85
<212> TYPE: DNA
<213> ORGANISM: Unknown
<220> FEATURE:
<223> OTHER INFORMATION: Solanaceae

<400> SEQUENCE: 25
gatttcgaca aattgcaact ggtattaaca tggccaccat catcagatgg atcctgatat  60
caagtgtact gaaggagcac cggaa                                        85

<210> SEQ ID NO 26
<211> LENGTH: 85
<212> TYPE: DNA
<213> ORGANISM: Unknown
<220> FEATURE:
<223> OTHER INFORMATION: Solanaceae
<220> FEATURE:
<221> NAME/KEY: misc_feature
<222> LOCATION: (27)..(68)
<223> OTHER INFORMATION: n is a, c, g, or t

<400> SEQUENCE: 26
gatttcgaca aattgcaact ggtattnnnn nnnnnnnnnn nnnnnnnnnn nnnnnnnnn   60 nnnnnnnnct gaaggagcac cggaa                                        85

<210> SEQ ID NO 27
<211> LENGTH: 40
<212> TYPE: DNA
<213> ORGANISM: Unknown
<220> FEATURE:
<223> OTHER INFORMATION: Solanaceae

<400> SEQUENCE: 27
gatttcgaca aattgcaact ggtctgaagg agcaccggaa                        40

<210> SEQ ID NO 28
<211> LENGTH: 78
<212> TYPE: DNA
<213> ORGANISM: Unknown
<220> FEATURE:
<223> OTHER INFORMATION: Solanaceae

<400> SEQUENCE: 28
gatttcgaca aattgcaact ggtacatggc caccatcatc agatggatcc tgatatcaag  60
tgtgaaggag caccggaa                                                78

<210> SEQ ID NO 29
<211> LENGTH: 38
<212> TYPE: DNA
<213> ORGANISM: Unknown
<220> FEATURE:
<223> OTHER INFORMATION: Solanaceae

<400> SEQUENCE: 29
gatttcgaca aattgcaact ggtgaaggag caccggaa                          38

<210> SEQ ID NO 30
<211> LENGTH: 42
<212> TYPE: DNA
<213> ORGANISM: Unknown
<220> FEATURE:
<223> OTHER INFORMATION: Solanaceae
```

```
<400> SEQUENCE: 30
cagatggatc ctgatatcaa gtgtactgaa ggagcaccgg aa                          42

<210> SEQ ID NO 31
<211> LENGTH: 43
<212> TYPE: DNA
<213> ORGANISM: Unknown
<220> FEATURE:
<223> OTHER INFORMATION: Solanaceae

<400> SEQUENCE: 31
gatttcgaca aattgcaact ggtattctga aggagcaccg gaa                         43

<210> SEQ ID NO 32
<211> LENGTH: 26
<212> TYPE: DNA
<213> ORGANISM: Unknown
<220> FEATURE:
<223> OTHER INFORMATION: Solanaceae

<400> SEQUENCE: 32
gatttcgaca aattgcaact ggtatt                                            26

<210> SEQ ID NO 33
<211> LENGTH: 23
<212> TYPE: DNA
<213> ORGANISM: Unknown
<220> FEATURE:
<223> OTHER INFORMATION: Solanaceae

<400> SEQUENCE: 33
gatttcctga aggagcaccg gaa                                               23

<210> SEQ ID NO 34
<211> LENGTH: 216
<212> TYPE: PRT
<213> ORGANISM: Unknown
<220> FEATURE:
<223> OTHER INFORMATION: Solanaceae

<400> SEQUENCE: 34
```

Met Phe Lys Ser Leu Leu Thr Ser Thr Leu Phe Ile Val Leu Phe Ser
1               5                   10                  15

Leu Ser Ser Thr Tyr Ala Asp Phe Asp Lys Leu Gln Leu Val Leu Thr
            20                  25                  30

Trp Pro Pro Ser Phe Cys His Ala Asn Ser Cys Gln Arg Ile Val Pro
        35                  40                  45

Lys Asn Phe Thr Ile His Gly Leu Trp Pro Asp Lys Glu Gly Pro Gln
    50                  55                  60

Leu Leu Lys Tyr Cys Lys Pro Lys Leu Lys Tyr Asn Tyr Phe Ser Asp
65                  70                  75                  80

Lys Met Leu Asn Asp Leu Asp Lys His Trp Ile Gln Leu Lys Val Asp
                85                  90                  95

Gln Ala Ser Ala Leu Lys Asp Gln Arg Ala Trp Lys Tyr Gln Tyr Leu
            100                 105                 110

Lys His Gly Ser Cys Cys Gln Lys Ile Tyr Asn Gln Asn Thr Tyr Phe
        115                 120                 125

Ser Leu Ala Leu His Leu Lys Asp Arg Phe Asp Leu Leu Arg Thr Leu
    130                 135                 140

Gln Ile His Arg Ile Val Pro Gly Ser Ser Tyr Thr Phe Glu Glu Ile

```
                145                 150                 155                 160
Val Asp Ala Val Lys Thr Val Thr Gln Met Asp Pro Asp Ile Lys Cys
                    165                 170                 175

Thr Glu Gly Ala Pro Glu Leu Tyr Glu Ile Gly Ile Cys Phe Thr Pro
                    180                 185                 190

Asn Gly Asp Ser Leu Val Gly Cys Arg Gln Ser Glu Thr Cys Asp Lys
                    195                 200                 205

Thr Gly Lys Ile Phe Phe Arg Pro
                    210                 215

<210> SEQ ID NO 35
<211> LENGTH: 202
<212> TYPE: PRT
<213> ORGANISM: Unknown
<220> FEATURE:
<223> OTHER INFORMATION: Solanaceae
<220> FEATURE:
<221> NAME/KEY: misc_feature
<222> LOCATION: (202)..(202)
<223> OTHER INFORMATION: Xaa can be any naturally occurring amino acid

<400> SEQUENCE: 35

Met Val Lys Pro Gln Leu Thr Ser Ala Leu Phe Ile Val Leu Phe Ala
1               5                   10                  15

Leu Ser Pro Ala Tyr Gly Asp Phe Asp Ser Leu Gln Leu Val Leu Thr
                20                  25                  30

Trp Pro Ala Ser Phe Cys His Val Asn Asp Cys Val Arg Ile Ala Pro
            35                  40                  45

Lys Asn Phe Thr Ile His Gly Leu Trp Pro Asp Lys Glu Gly Thr Val
    50                  55                  60

Leu Gln Asn Cys Lys Pro Lys Pro Lys Tyr Val Asn Phe Lys Asp Lys
65                  70                  75                  80

Met Phe Asn Asp Leu Asp Lys His Trp Ile Gln Leu Lys Phe Asp Glu
                85                  90                  95

Asp Tyr Gly Glu Lys Glu Gln Pro Leu Trp Leu Tyr Gln Tyr Phe Lys
                100                 105                 110

His Gly Ser Cys Cys Gln Lys Met Tyr Asn Gln Asn Thr Tyr Phe Ser
            115                 120                 125

Leu Ala Leu Arg Leu Lys Asp Arg Phe Asp Leu Leu Arg Thr Leu Gln
    130                 135                 140

Ile His His Ile Phe Pro Gly Ser Ser Tyr Thr Phe Lys Lys Ile Phe
145                 150                 155                 160

Asp Ala Val Lys Thr Ala Thr Gln Met Asp Pro Asp Leu Lys Cys Thr
                165                 170                 175

Lys Gly Val Pro Glu Leu Tyr Glu Ile Gly Ile Cys Phe Thr Pro Asn
                180                 185                 190

Ala Asp Ala Leu Ile Pro Cys Arg Gln Xaa
            195                 200

<210> SEQ ID NO 36
<211> LENGTH: 216
<212> TYPE: PRT
<213> ORGANISM: Unknown
<220> FEATURE:
<223> OTHER INFORMATION: Solanaceae

<400> SEQUENCE: 36

Met Phe Lys Ser Leu Leu Thr Ser Thr Leu Phe Ile Val Leu Phe Tyr
1               5                   10                  15
```

Leu Ser Ser Thr Tyr Ala Asp Phe Asp Lys Leu Gln Leu Val Leu Thr
            20                  25                  30

Trp Pro Pro Ser Phe Cys His Ala Asn Ser Cys Gln Arg Ile Val Pro
        35                  40                  45

Lys Asn Phe Thr Ile His Gly Leu Trp Pro Asp Lys Glu Gly Pro Gln
    50                  55                  60

Leu Leu Lys Tyr Cys Lys Pro Lys Leu Lys Tyr Lys Tyr Phe Ser Asp
65                  70                  75                  80

Lys Met Phe Asn Asp Leu Asp Lys His Trp Ile Gln Leu Lys Phe Asp
                85                  90                  95

Glu Asp Ser Ala Leu Lys Asp Gln Arg Ala Trp Lys Tyr Gln Tyr Leu
            100                 105                 110

Lys His Gly Ser Cys Cys Gln Lys Met Tyr Asn Gln Asn Thr Tyr Phe
        115                 120                 125

Ser Leu Ala Leu Arg Leu Lys Asp Arg Phe Asp Leu Leu Arg Thr Leu
    130                 135                 140

Gln Ile His His Ile Phe Pro Gly Ser Ser Tyr Thr Phe Glu Glu Ile
145                 150                 155                 160

Val Asp Ala Val Lys Thr Val Thr Gln Met Asp Pro Asp Ile Lys Cys
                165                 170                 175

Thr Glu Gly Ala Pro Glu Leu Tyr Glu Ile Gly Ile Cys Phe Thr Pro
            180                 185                 190

Asn Gly Asp Ser Leu Val Gly Cys Arg Gln Ser Glu Thr Cys Asp Lys
        195                 200                 205

Thr Gly Lys Ile Phe Phe Arg Pro
    210                 215

<210> SEQ ID NO 37
<211> LENGTH: 216
<212> TYPE: PRT
<213> ORGANISM: Unknown
<220> FEATURE:
<223> OTHER INFORMATION: Solanaceae

<400> SEQUENCE: 37

Met Phe Lys Ser Leu Leu Thr Ser Thr Leu Phe Ile Val Leu Phe Tyr
1               5                   10                  15

Leu Ser Ser Thr Tyr Ala Asp Phe Asp Lys Leu Gln Leu Val Leu Thr
            20                  25                  30

Trp Pro Pro Ser Phe Cys His Ala Asn Ser Cys Gln Arg Ile Val Pro
        35                  40                  45

Lys Asn Phe Thr Ile His Gly Leu Trp Pro Asp Lys Glu Gly Pro Gln
    50                  55                  60

Leu Leu Lys Tyr Cys Lys Pro Lys Leu Lys Tyr Lys Tyr Phe Ser Asp
65                  70                  75                  80

Lys Met Phe Asn Asp Leu Asp Lys His Trp Ile Gln Leu Lys Phe Asp
                85                  90                  95

Glu Asp Ser Ala Leu Lys Asp Gln Arg Ala Trp Lys Tyr Gln Tyr Leu
            100                 105                 110

Lys His Gly Ser Cys Cys Gln Lys Met Tyr Asn Gln Asn Thr Tyr Phe
        115                 120                 125

Ser Leu Ala Leu Arg Leu Lys Asp Arg Phe Asp Leu Leu Arg Thr Leu
    130                 135                 140

Gln Ile His His Ile Phe Pro Gly Ser Ser Tyr Thr Phe Glu Glu Ile
145                 150                 155                 160

```
Val Asp Ala Val Lys Thr Val Thr Gln Met Asp Pro Asp Ile Lys Cys
            165                 170                 175

Thr Glu Gly Ala Pro Glu Leu Tyr Glu Ile Gly Ile Cys Phe Thr Pro
        180                 185                 190

Asn Gly Asp Ser Leu Val Gly Cys Arg Gln Ser Glu Thr Cys Asp Lys
        195                 200                 205

Thr Gly Lys Ile Phe Phe Arg Pro
    210                 215

<210> SEQ ID NO 38
<211> LENGTH: 81
<212> TYPE: DNA
<213> ORGANISM: Unknown
<220> FEATURE:
<223> OTHER INFORMATION: Solanaceae

<400> SEQUENCE: 38
atttcgacaa attgcaactg gtattaacat ggccaccatc aagatggatc ctgatatcaa      60
gtgtactgaa ggagcaccgg a                                               81

<210> SEQ ID NO 39
<211> LENGTH: 38
<212> TYPE: DNA
<213> ORGANISM: Unknown
<220> FEATURE:
<223> OTHER INFORMATION: Solanaceae

<400> SEQUENCE: 39
atttcgacaa attgcaactg gtctgaagga gcaccgga                             38

<210> SEQ ID NO 40
<211> LENGTH: 81
<212> TYPE: DNA
<213> ORGANISM: Unknown
<220> FEATURE:
<223> OTHER INFORMATION: Solanaceae

<400> SEQUENCE: 40
atttcgacaa attgcaactg gtattagata tcaggatcca ttggcaaaat gatggtggcc     60
atgttctgaa ggagcaccgg a                                               81

<210> SEQ ID NO 41
<211> LENGTH: 38
<212> TYPE: DNA
<213> ORGANISM: Unknown
<220> FEATURE:
<223> OTHER INFORMATION: Solanaceae

<400> SEQUENCE: 41
atttcgacaa attgcaactg gtctgaagga gcaccgga                             38

<210> SEQ ID NO 42
<211> LENGTH: 74
<212> TYPE: DNA
<213> ORGANISM: Unknown
<220> FEATURE:
<223> OTHER INFORMATION: Solanaceae

<400> SEQUENCE: 42
atttcgacaa attgcaactg gtacatggcc accatcaaga tggatcctga tatcaagtgt     60
gaaggagcac cgga                                                       74
```

<210> SEQ ID NO 43
<211> LENGTH: 81
<212> TYPE: DNA
<213> ORGANISM: Unknown
<220> FEATURE:
<223> OTHER INFORMATION: Solanaceae

<400> SEQUENCE: 43
atttcgacaa attgcaactg gtattaaaca tggccaccat cagatggatc ctgatatcaa    60
gtgtactgaa ggagcaccgg a                                              81

<210> SEQ ID NO 44
<211> LENGTH: 21
<212> TYPE: DNA
<213> ORGANISM: Unknown
<220> FEATURE:
<223> OTHER INFORMATION: Solanaceae

<400> SEQUENCE: 44
atttcgacaa attgcaactg g                                              21

<210> SEQ ID NO 45
<211> LENGTH: 42
<212> TYPE: DNA
<213> ORGANISM: Unknown
<220> FEATURE:
<223> OTHER INFORMATION: Solanaceae

<400> SEQUENCE: 45
tcagatggat cctgatatca agtgtactga aggagcaccg ga                       42

<210> SEQ ID NO 46
<211> LENGTH: 37
<212> TYPE: DNA
<213> ORGANISM: Unknown
<220> FEATURE:
<223> OTHER INFORMATION: Solanaceae

<400> SEQUENCE: 46
atttcgacaa attgcaactg gtacatggcc accatca                             37

<210> SEQ ID NO 47
<211> LENGTH: 74
<212> TYPE: DNA
<213> ORGANISM: Unknown
<220> FEATURE:
<223> OTHER INFORMATION: Solanaceae

<400> SEQUENCE: 47
atttcgacaa attgcaactg gtacatggcc accatcaaga tggatcctga tatcaagtgt    60
gaaggagcac cgga                                                      74

<210> SEQ ID NO 48
<211> LENGTH: 79
<212> TYPE: DNA
<213> ORGANISM: Unknown
<220> FEATURE:
<223> OTHER INFORMATION: Solanaceae

<400> SEQUENCE: 48
atttcgacaa attgcaactg gtattacatg gccaccatca agatggatcc tgatatcaag    60
tgtctgaagg agcaccgga                                                 79

```
<210> SEQ ID NO 49
<211> LENGTH: 42
<212> TYPE: DNA
<213> ORGANISM: Unknown
<220> FEATURE:
<223> OTHER INFORMATION: Solanaceae

<400> SEQUENCE: 49
atttcgacaa attgcaactg gtattactga aggagcaccg ga                          42

<210> SEQ ID NO 50
<211> LENGTH: 30
<212> TYPE: DNA
<213> ORGANISM: Unknown
<220> FEATURE:
<223> OTHER INFORMATION: Solanaceae

<400> SEQUENCE: 50
atttcgacaa attgcaactg gccaccatca                                        30

<210> SEQ ID NO 51
<211> LENGTH: 67
<212> TYPE: DNA
<213> ORGANISM: Unknown
<220> FEATURE:
<223> OTHER INFORMATION: Solanaceae

<400> SEQUENCE: 51
atttcgacaa attgcaactg gccaccatca agatggatcc tgatatcaag tctgaaggag       60
caccgga                                                                 67

<210> SEQ ID NO 52
<211> LENGTH: 245
<212> TYPE: PRT
<213> ORGANISM: Unknown
<220> FEATURE:
<223> OTHER INFORMATION: Solanaceae

<400> SEQUENCE: 52
```

Met Phe Lys Ser Leu Leu Thr Ser Thr Leu Phe Ile Val Leu Phe Ser
1               5                  10                  15

Leu Ser Ser Thr Tyr Gly Asp Phe Asp Lys Leu Gln Leu Val Leu Thr
            20                  25                  30

Trp Pro Pro Ser Phe Cys His Ala Asn Asn Cys Gln Arg Ile Val Pro
        35                  40                  45

Lys Asn Phe Thr Ile His Gly Leu Trp Pro Asp Lys Glu Gly Pro Gln
    50                  55                  60

Leu Leu Lys Tyr Cys Lys Pro Lys Leu Thr Tyr Asn Tyr Phe Ser Val
65                  70                  75                  80

Ser Ser Phe Ile Ile Phe Phe Arg Thr Gly Ser Phe Ser Val Leu Phe
                85                  90                  95

Asn Leu Leu Lys Ser Leu Phe Phe Asn Phe Leu Gln Asp Lys Met Leu
            100                 105                 110

Asn Asp Leu Asp Lys His Trp Ile Gln Leu Lys Ile Asp Gln Ala Ser
        115                 120                 125

Ala Arg Lys Asp Gln Pro Ala Trp Lys Tyr Tyr Leu Lys His Gly
    130                 135                 140

Ser Cys Cys Gln Lys Ile Tyr Asn Gln Asn Thr Tyr Phe Ser Leu Ala
145                 150                 155                 160

Leu Arg Leu Lys Asp Arg Phe Asp Leu Leu Arg Thr Leu Gln Ile His
                165                 170                 175

Arg Ile Val Pro Gly Ser Ser Tyr Thr Phe Glu Ile Phe Asp Ala
            180                 185                 190

Val Lys Thr Val Thr Gln Met Asp Pro Asp Ile Lys Cys Thr Glu Gly
            195                 200                 205

Ala Pro Glu Leu Tyr Glu Ile Gly Ile Cys Phe Thr Pro Asn Gly Asp
        210                 215                 220

Ser Leu Val Arg Cys Arg Gln Ser Glu Thr Cys Asp Lys Thr Gly Lys
225                 230                 235                 240

Ile Phe Phe Arg Pro
                245

<210> SEQ ID NO 53
<211> LENGTH: 245
<212> TYPE: PRT
<213> ORGANISM: Unknown
<220> FEATURE:
<223> OTHER INFORMATION: Solanaceae

<400> SEQUENCE: 53

Met Phe Lys Ser Leu Leu Thr Ser Thr Leu Phe Ile Val Leu Phe Tyr
1               5                   10                  15

Leu Ser Ser Thr Tyr Ala Asp Phe Asp Lys Leu Gln Leu Val Leu Thr
            20                  25                  30

Trp Pro Pro Ser Phe Cys His Ala Asn Ser Cys Gln Arg Ile Val Pro
        35                  40                  45

Lys Asn Phe Thr Ile His Gly Leu Trp Pro Asp Lys Glu Gly Pro Gln
50                  55                  60

Leu Leu Lys Tyr Cys Lys Pro Lys Leu Lys Tyr Lys Tyr Phe Ser Val
65                  70                  75                  80

Asn Ser Phe Ile Ile Phe Phe Arg Thr Gly Ser Phe Ser Ile Leu Phe
                85                  90                  95

Asn Leu Val Lys Arg Leu Phe Leu Asn Phe Leu Gln Asp Lys Met Phe
            100                 105                 110

Asn Asp Leu Asp Lys His Trp Ile Gln Leu Lys Phe Asp Glu Asp Ser
        115                 120                 125

Ala Leu Lys Asp Gln Arg Ala Trp Lys Tyr Gln Tyr Leu Lys His Gly
    130                 135                 140

Ser Cys Cys Gln Lys Met Tyr Asn Gln Asn Thr Tyr Phe Ser Leu Ala
145                 150                 155                 160

Leu Arg Leu Lys Asp Arg Phe Asp Leu Leu Arg Thr Leu Gln Ile His
                165                 170                 175

His Ile Phe Pro Gly Ser Ser Tyr Thr Phe Glu Glu Ile Val Asp Ala
            180                 185                 190

Val Lys Thr Val Thr Gln Met Asp Pro Asp Ile Lys Cys Thr Glu Gly
        195                 200                 205

Ala Pro Glu Leu Tyr Glu Ile Gly Ile Cys Phe Thr Pro Asn Gly Asp
    210                 215                 220

Ser Leu Val Gly Cys Arg Gln Ser Glu Thr Cys Asp Lys Thr Gly Lys
225                 230                 235                 240

Ile Phe Phe Arg Pro
                245

<210> SEQ ID NO 54
<211> LENGTH: 245
<212> TYPE: PRT
<213> ORGANISM: Unknown

```
<220> FEATURE:
<223> OTHER INFORMATION: Solanaceae

<400> SEQUENCE: 54

Met Phe Lys Ser Leu Leu Thr Ser Thr Leu Phe Ile Val Leu Phe Ser
1               5                   10                  15

Leu Ser Ser Thr Tyr Ala Asp Phe Asp Lys Leu Gln Leu Val Leu Thr
            20                  25                  30

Trp Pro Pro Ser Phe Cys His Ala Asn Ser Cys Gln Arg Ile Val Pro
            35                  40                  45

Lys Asn Phe Thr Ile His Gly Leu Trp Pro Asp Lys Glu Gly Pro Gln
            50                  55                  60

Leu Leu Lys Tyr Cys Lys Pro Lys Leu Lys Tyr Asn Tyr Phe Ser Val
65                  70                  75                  80

Asn Ser Phe Ile Ile Phe Phe Arg Thr Gly Ser Phe Ser Ile Leu Phe
                85                  90                  95

Asn Leu Val Lys Arg Leu Phe Leu Asn Phe Leu Gln Asp Lys Met Leu
                100                 105                 110

Asn Asp Leu Asp Lys His Trp Ile Gln Leu Lys Val Asp Gln Ala Ser
            115                 120                 125

Ala Leu Lys Asp Gln Arg Ala Trp Lys Tyr Gln Tyr Leu Lys His Gly
        130                 135                 140

Ser Cys Cys Gln Lys Ile Tyr Asn Gln Asn Thr Tyr Phe Ser Leu Ala
145                 150                 155                 160

Leu His Leu Lys Asp Arg Phe Asp Leu Leu Arg Thr Leu Gln Ile His
                165                 170                 175

Arg Ile Val Pro Gly Ser Ser Tyr Thr Phe Glu Glu Ile Val Asp Ala
            180                 185                 190

Val Lys Thr Val Thr Gln Met Asp Pro Asp Ile Lys Cys Thr Glu Gly
        195                 200                 205

Ala Pro Glu Leu Tyr Glu Ile Gly Ile Cys Phe Thr Pro Asn Gly Asp
    210                 215                 220

Ser Leu Val Gly Cys Arg Gln Ser Glu Thr Cys Asp Lys Thr Gly Lys
225                 230                 235                 240

Ile Phe Phe Arg Pro
            245
```

OVERCOMING SELF-INCOMPATIBILITY IN DIPLOID PLANTS FOR BREEDING AND PRODUCTION OF HYBRIDS

CROSS REFERENCE TO RELATED APPLICATIONS

This is a National Phase application claiming priority to PCT/US2019/041993 filed Jul. 16, 2019, which claims priority under 35 U.S.C. § 119 to provisional application U.S. Ser. No. 62/698,363, filed Jul. 16, 2018, all of which are herein incorporated by reference in their entirety.

SEQUENCE LISTING

The instant application contains a sequence listing, which has been submitted in ASCII format by electronic submission and is hereby incorporated by reference in its entirety. Said ASCII copy, created on Aug. 25, 2021, is named P12650US01_ST25.txt and is 36,864 bytes in size.

FIELD OF THE INVENTION

The invention relates generally to the field of molecular biology and plant genetics.

BACKGROUND OF THE INVENTION

Potato breeding programs rely on the discovery and introgression of genes of interest. However, the polyploid nature of potatoes hampers the fixation of desirable alleles in new cultivars. Therefore, creating inbred diploid potatoes represents an alternative strategy for obtaining homozygous lines.

Diploid potatoes, however, possess self-incompatibility (SI) that forces outcrossing and limits potato inbred line development. In the gametophytic SI system, characteristic of the Solanaceae family, the S-locus F-box protein expressed in the pollen does not recognize its own S haplotype of the style (S-RNAse), expressed in the pistil, inhibiting the elongation of self-pollen tubes by degrading RNA.

SUMMARY OF THE INVENTION

Applicants have surprisingly found that modulation of S RNAse locus can avoid self-pollen inactivation. The invention provides methods for creating hybrid plants and inbred lines by modulating of this locus and plants produced by such methods.

The present invention provides a method for genetic modification of plants to reduce or eliminate self-incompatibility. Using the methods and materials of the present invention, self-incompatibility may be induced, increased, decreased, repressed or otherwise altered, in a transformed plant relative to an untransformed control plant, for example by incorporating additional copies of a sense nucleic acid of the present invention, preferably to overexpress the polypeptide or in sense suppression. They may be decreased or otherwise altered, for example by incorporating an antisense nucleic acid of the present invention or preferably by chromosomal insertion or deletion of sequences through the use of gene editing techniques.

In a further aspect, the present invention provides a method for altering the self-incompatibility status of a plant, said method including identifying a gene encoding an S RNAse polypeptide which is active in the self-incompatibility pathway of the plant and up-regulating or down-regulating expression of said gene to repress or induce the self-incompatibility mechanism in said plant. Preferably said gene is a nucleic acid according to the present invention. Preferably the plant is as hereinbefore described. The up-regulation or down-regulation may be carried out by methods known to those skilled in the art. For example, a gene may be upregulated by incorporating additional copies of a sense copy of the gene. A gene may be down-regulated, for example, by incorporating an antisense nucleic acid, a frame-shifted or otherwise modified sense copy of the gene, or nucleic acid encoding interfering RNA (RNAi). Up or down regulation may also be achieved through the use of transcription activator-like effector nucleases or zinc-finger nucleases, mediating cleavage of specific target sites in the nucleic acid, leading to micro-deletions and insertions within the endogenous nucleic acid sequence. One of several genome modification techniques such as genome editing technologies, including but not limited to RTDS, TALEN, CRISPR-Cas9, CRISPR-Cmsl, ARCUS or base editing, chemical mutagenesis, RNAi, antisense etc. may be used to introduce a deletion, insertion, or substitution in an S RNAse gene to lead to the reduction or elimination of the R RNAse activity, thereby reducing the level of functionally active endogenous S RNASe and reducing and/or preventing activation of self-incompatibility. Applicants have a targeted knock-out of the S-RNase locus in self-incompatibility potato lines using Clustered Regularly Interspaced Short Palindromic Repeats/CRISPR-associated systems (CRISPR/Cas9) technology in an effort to avoid self-pollen inactivation. A number of indels were generated with inactivated S RNAse activity (SEQ NOS: 5-21, 26-34, and 40-53)

Techniques for incorporating the genetic constructs of the present invention into plant cells are known to those skilled in the art. Such techniques include high velocity projectile introduction to cells, tissues, calli, immature and mature embryos. Cells incorporating the genetic constructs of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced either sexually or asexually, using methods well known in the art.

The invention further provides a Solanaceae plant, plant part, plant organ, plant cell or seed, obtainable according to the methods according to the invention, wherein the expression and/or activity of an S RNAse gene and/or protein has been altered as compared to a control plant. Also provided is a Solanaceae plant comprising a mutant allele of an S RNAse gene, said mutant allele resulting in an alteration of the expression and/or activity of the S RNAse protein encoded by said gene compared to a plant not comprising said mutation in which, self-incompatibility has been modulated compared to said plant not comprising said mutation.

Further provided is a method for identifying a Solanaceae plant, such as a potato plant, with a modulated self-incompatibility comprising the step of providing a population of Solanaceae plants, for example a population that has been subjected to mutagenesis, b. identifying one or more plants with a mutant allele of an S RNAse gene, such as an S RNAse gene having at least 80% sequence identity to any one of SEQ ID NOs: 1, 2 or 3, or an S RNAse gene encoding a protein having at least 80% sequence identity to any one of SEQ ID NOs: 54, 55, or 56, and identifying within said plants with a mutant allele of an S RNAse gene, one or more plants that have a modulated self-incompatibility compared to a plant of the same species not comprising said mutation.

Detection of expression products is performed either qualitatively (by detecting presence or absence of one or more product of interest) or quantitatively (by monitoring the level of expression of one or more product of interest). In one embodiment, the expression product is an RNA expression product. Aspects of the invention optionally include monitoring an expression level of a nucleic acid, polypeptide or chemical) as noted herein for detection of S RNAse which encode proteins which inhibit the elongation of self-pollen tubes in a plant or in a population of plants.

By 'repressing the self-incompatibility mechanism' of a plant is meant reducing the tendency of the plant to inhibit pollen tube elongation and resulting fertilization of self-pollen.

By 'activating the self-incompatibility mechanism' of a plant is meant introducing the tendency of the plant to inhibit pollen tube elongation and resulting fertilization of self-pollen.

In a further aspect, the present invention provides a substantially purified or isolated nucleic acid or nucleic acid fragment encoding a plant self-incompatibility (self-incompatibility) protein, complements thereof, sequences antisense thereto, and functionally active fragments and variants thereof. Preferably, the nucleic acid or nucleic acid fragment encodes a polypeptide selected from the group consisting of and S-RNAse protein as described herein.

In a preferred embodiment, the present invention provides a substantially purified or isolated nucleic acid or nucleic acid fragment encoding an S RNAse including a nucleotide sequence selected from the group consisting of: (a) the sequences shown in SEQ ID NO: 1, 2, or 3 (b) a nucleotide sequence encoding the polypeptide shown SEQ ID NO: 54, 55, or 56; (c) complements of the sequences recited in (a) and (b); (d) sequences antisense to the sequences recited in (a) and (b); (e) functionally active fragments of the sequences recited in (a), (b), (c) and (d); and (0 functionally active variants of the sequences recited in (a), (b), (c), (d) and (e).

The nucleic acid or nucleic acid fragment may be isolated from or correspond to a gene from a plant of the Solanaceae family. According to the invention a method of modulating the S-RNAse pathway comprises modulating the activity of one or more S-RNAse genes in the plant, wherein the one or more S-RNAse genes encode one or more S-RNAses, wherein at least one of the one or more S-RNAse genes comprises, e.g., at least about 70%, at least about 75%, at least about 80%, at least about 85%, at least about 90%, at least about 95%, at least about 99%, at least about 99.5% or more sequence identity to SEQ ID NOS: 1, 2, or 3.

In another embodiment, the modulating comprises: (a) introducing into the plant at least one polynucleotide sequence, wherein the at least one polynucleotide sequence comprises a nucleic acid encoding one or more S-RNAse genes, or a subsequence thereof, and a heterologous promoter, which promoter functions in plants and/or, (b) expressing at least one polynucleotide sequence, thereby modulating (decreasing) the activity of one or more S-RNAse native genes compared to a corresponding control plant (e.g., its non-transgenic parent or a non-transgenic plant of the same species). For example, the at least one polynucleotide sequence can be introduced by techniques including, but not limited to, electroporation, micro-projectile bombardment, *Agrobacterium*-mediated transfer, and the like. In certain other embodiments, gene editing protocols may be used to modulate (decrease) activity of S-RNAse genes as disclosed herein. Essentially all of the features noted above apply to this embodiment as well.

Novel S-RNAse sequences have been identified for use in modulating S RNAse activity. According to an aspect of some embodiments of the present invention there is provided an isolated polynucleotide comprising a nucleic acid sequence at least 80% identical to SEQ ID NO: 1, 2, or 3, wherein said nucleic acid sequence is capable producing cytotoxic effects that inhibit the elongation of pollen tubes by degrading RNA and thereby producing self-incompatibility.

According to some embodiments of the invention, the plant cell forms part of a plant.

DETAILED DESCRIPTION OF THE INVENTION

Figure 1:
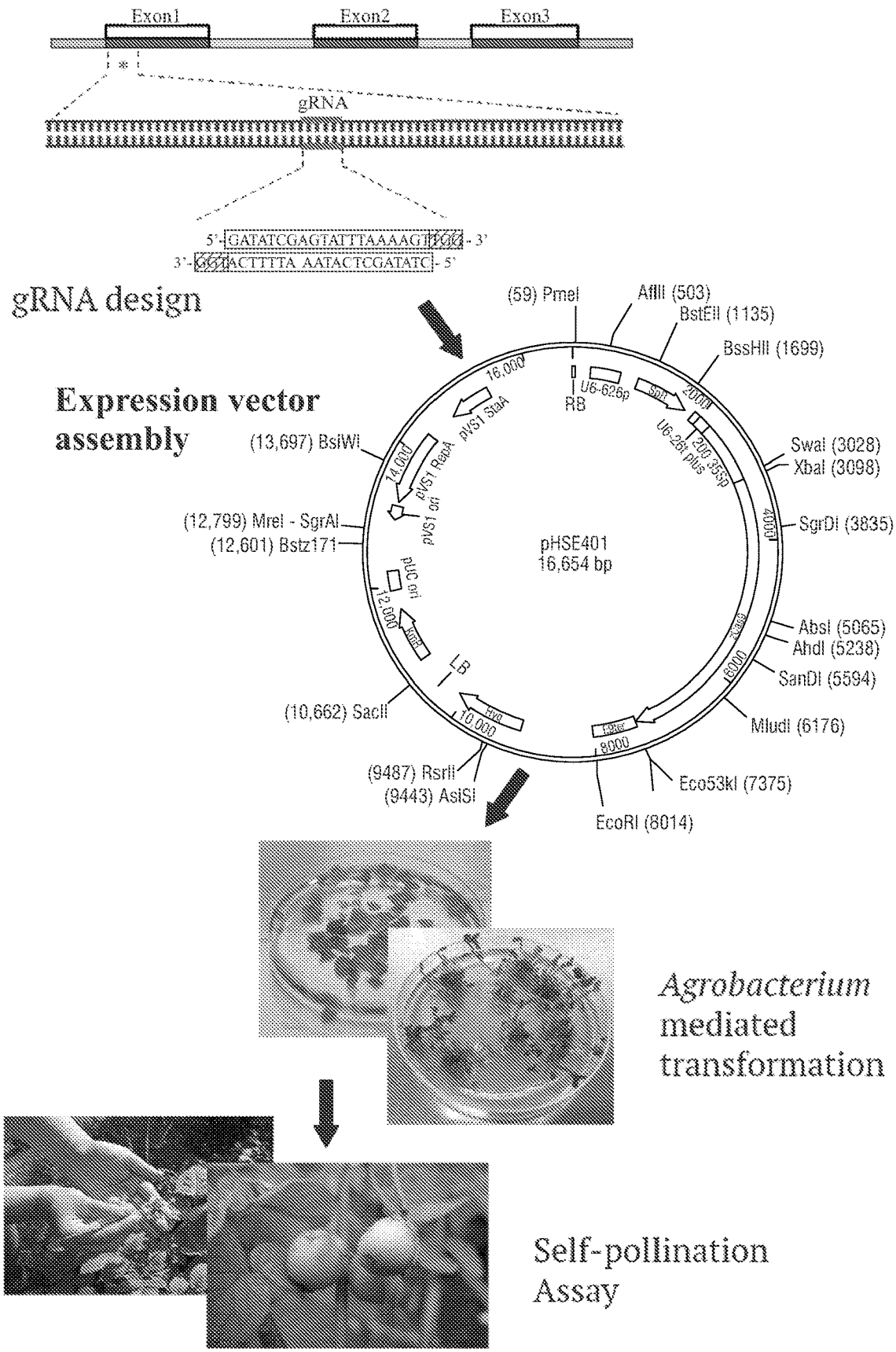
FIG. 1. Single guide RNA (sgRNA) selection, assembly, and S-RNAse knock-out generation. pHSE401 was a gift from Qi-Jun Chen (Addgene plasmid #62201)

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5$^{th}$ ed., Prentice-Hall; Dhringra and Sinclair, (1985) *Basic Plant Pathology Methods*, CRC Press; Maniatis, et al., (1982) *Molecular Cloning: A Laboratory Manual*; *DNA Cloning*, vols. I and II, Glover, ed. (1985); *Oligonucleotide Synthesis*, Gait, ed. (1984); *Nucleic Acid Hybridization*, Hames and Higgins, eds. (1984); and the series *Methods in Enzymology*, Colowick and Kaplan, eds, Academic Press, Inc., San Diego, CA.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence-based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Persing, et al., eds., American Society for Microbiology, Washington, DC (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins*, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) *Proc. Natl. Acad. Sci. USA* 82:2306-9), or the ciliate Macronucleus, may be used when the nucleic acid is expressed using these organisms.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, lawn grass, barley, millet, potato and tomato. Particularly preferred are polyploid plants that possess self-incompatibility.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" or "isolated nucleic acid" or "isolated protein" refer to material, such as a nucleic acid or a protein, which is substantially or essentially free from components which normally accompany or interact with it as found in its naturally occurring environment. The isolated material optionally comprises material not found with the material in its natural environment. Nucleic acids which are "isolated", as defined herein, are also referred to as "heterologous" nucleic acids. Unless otherwise stated, the term "S-RNAse nucleic acid" means a nucleic acid comprising a polynucleotide ("S-RNAse polynucleotide") encoding a full length or partial length S-RNAse polypeptide with S-RNAse activity as defined herein.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, CA; Sambrook, et al., (1989) *Molecular Cloning: A Laboratory Manual,* $2^{nd}$ ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, cells in or from seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium,* and *Triticum*. A particularly preferred plant is *Solanum tuberosum*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "S-RNAse polypeptide" refers to one or more amino acid sequences. The term is also inclusive of fragments, variants, homologs, alleles or precursors (e.g., preproproteins or proproteins) thereof that retain the function of the gametophytic self-incompatibility system, characteristic of the Solanaceae family. More particularly, the characteristic of inhibiting the elongation of self-pollen tubes by degrading RNA. An "5-RNAse protein" comprises an S-RNAse polypeptide. Unless otherwise stated, the term "S-RNAse nucleic acid" means a nucleic acid comprising a polynucleotide ("S-RNAse polynucleotide") encoding an S-RNAse polypeptide.

As used herein "recombinant" includes reference to a cell or vector that has been modified by the introduction of a heterologous nucleic acid, or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "genetically modified plant" includes reference to a plant or ancestor thereof, to which has been introduced a heterologous polynucleotide. In some instances, the heterologous polynucleotide is stably integrated within the genome such that the polynucleotide is passed on to successive generations. In some instances, such as gene editing the heterologous polynucleotide engineers a chromosomal change that is passed to successive generations while the polynucleotide itself is not. The heterologous polynucleotide may be introduced alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by subsequent sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, and 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, California, GAP, BESTFIT, BLAST, FASTA, and TFASTA in the Wisconsin Genetics Software Package, Version 8 (available from Genetics Computer Group (GCG® programs (Accelrys, Inc., San Diego, CA).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, and 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, California, USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above, except that residue positions which are not identical may differ by conservative amino acid changes.

Nucleic Acids

The present invention provides, inter alia, isolated nucleic acids of RNA, DNA, homologs, paralogs and orthologs and/or chimeras thereof, comprising an S-RNAse polynucleotide. This includes naturally occurring as well as synthetic variants and homologs of the sequences.

Sequences homologous, i.e., that share significant sequence identity or similarity, to those provided herein derived from other plants of choice, are also an aspect of the invention. Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily related to crop plants, but which may not have yet been used as crop plants.

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

For example, a clade of very similar MADS domain transcription factors from Arabidopsis all share a common function in flowering time (Ratcliffe et al. (2001) Plant Physiol. 126: 122-132), and a group of very similar AP2 domain transcription factors from Arabidopsis are involved in tolerance of plants to freezing (Gilmour et al. (1998) Plant J. 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Variant Nucleotide Sequences in the Non-Coding Regions

The S-RNAse nucleotide sequences are used to generate variant nucleotide sequences having the nucleotide sequence of the 5'-untranslated region, 3'-untranslated region, or promoter region that is approximately 70%, 75%, and 80%, 85%, 90% and 95% identical to the original nucleotide sequence. These variants are then associated with natural variation in the germplasm for component traits related to self-fertility. The associated variants are used as marker haplotypes to select for the desirable traits.

Variant Amino Acid Sequences of Polypeptides

Variant amino acid sequences of the S-RNAse polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits. The associated variants are used as marker haplotypes to select for the desirable traits.

The present invention also includes polynucleotides optimized for expression in different organisms. For example, for expression of the polynucleotide in a particular plant, the sequence can be altered to account for specific codon.

The nucleic acids encoding S-RNAse peptides which may be used for the present invention comprise isolated S-RNAse polynucleotides which are inclusive of:
(a) a polynucleotide encoding an S-RNAse polypeptide and conservatively modified and polymorphic variants thereof;
(b) a polynucleotide having at least 70% sequence identity with polynucleotides of (a) or (b);
(c) Complementary sequences of polynucleotides of (a) or (b).

In certain embodiments the nucleic acids include at least one base substitution, insertion, or deletion so that they do not recite naturally occurring nucleic acid sequences.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers are well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMClneo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, CA); and, Amersham Life Sciences, Inc, Catalog '97 (Arlington Heights, IL).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G> 7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency or stop translation, and/or to optimize the coding sequence for expression in a desired host or to optimize the codon usage in a heterologous host. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics, and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present disclosure further provides recombinant expression cassettes comprising a nucleic acid of the present disclosure. A nucleic acid sequence coding for the desired polynucleotide of the present disclosure, for example a cDNA or a genomic sequence encoding a polypeptide long enough to code for an active protein of the present disclosure, can be used to construct a recombinant expression cassette which can be introduced into the desired host cell. A recombinant expression cassette will typically comprise a polynucleotide of the present disclosure operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

Promoters, Terminators, Introns

A plant promoter fragment can be employed which will direct expression of a polynucleotide of the present disclosure in essentially all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) Nature 313:810-2; rice actin (McElroy, et al., (1990) Plant Cell 163-171); ubiquitin (Christensen, et al., (1992) Plant Mol. Biol. 12:619-632 and Christensen, et al., (1992) Plant Mol. Biol. 18:675-89); pEMU (Last, et al., (1991) Theor. Appl. Genet. 81:581-8); MAS (Velten, et al., (1984) EMBO J. 3:2723-30) and maize H3 histone (Lepetit, et al., (1992) Mol. Gen. Genet. 231:276-85 and Atanassvoa, et al., (1992) Plant Journal 2(3):291-300); ALS promoter, as described in PCT Application Number WO 1996/30530 and other transcription initiation regions from various plant genes known to those of skill. For the present disclosure ubiquitin is the preferred promoter for expression in monocot plants.

Alternatively, the plant promoter can direct expression of a polynucleotide of the to present disclosure in a specific tissue or may be otherwise under more precise environmental or developmental control. Such promoters may be "inducible" promoters. Environmental conditions that may affect transcription by inducible promoters include pathogen attack, anaerobic conditions or the presence of light. Examples of inducible promoters are the Adhl promoter, which is inducible by hypoxia or cold stress, the Hsp70 promoter, which is inducible by heat stress and the PPDK promoter, which is inducible by light. Diurnal promoters that are active at different times during the circadian rhythm are also known (US Patent Application Publication Number 2011/0167517, incorporated herein by reference).

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) Nucleic Acids Res. 12:369-85); the potato proteinase inhibitor II (PINII) gene (Keil, et al., (1986) Nucleic Acids Res. 14:5641-50 and An, et al., (1989) Plant Cell 1:115-22) and the CaMV 19S gene (Mogen, et al., (1990) Plant Cell 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) Mol. Cell Biol. 8:4395-4405; Callis, et al., (1987) Genes Dev. 1:1183-200). Such intron enhancement of gene expression is typically greatest when placed near the 5' end of the transcription unit.

Signal Peptide Sequences

Plant signal sequences, including, but not limited to, signal-peptide encoding DNA/RNA sequences which target proteins to the extracellular matrix of the plant cell (Dratewka-Kos, et al., (1989) J. Biol. Chem. 264:4896-900), such as the *Nicotiana plumbaginifolia* extension gene (DeLoose, et al., (1991) Gene 99:95-100); signal peptides which target proteins to the vacuole, such as the sweet potato sporamin gene (Matsuka, et al., (1991) Proc. Natl. Acad. Sci. USA 88:834) and the barley lectin gene (Wilkins, et al., (1990) Plant Cell, 2:301-13); signal peptides which cause proteins to be secreted, such as that of PRIb (Lind, et al., (1992) Plant Mol. Biol. 18:47-53) or the barley alpha amylase (BAA) (Rahmatullah, et al., (1989) Plant Mol. Biol. 12:119) or signal peptides which target proteins to the plastids such as that of rapeseed enoyl-Acp reductase (Verwaert, et al., (1994) Plant Mol. Biol. 26:189-202) are useful in the disclosure.

Markers

The vector comprising the sequences from a polynucleotide of the present disclosure will typically comprise a marker gene, which confers a selectable phenotype on plant cells. The selectable marker gene may encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Also useful are genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Constructs described herein may comprise a polynucleotide of interest encoding a reporter or marker product. Examples of suitable reporter polynucleotides known in the art can be found in, for example, Jefferson, et al., (1991) in Plant Molecular Biology Manual, ed. Gelvin, et al., (Kluwer Academic Publishers), pp. 1-33; DeWet, et al. (1987) Mol. Cell. Biol. 7:725-737; Goff, et al., (1990) EMBO J. 9:2517-2522; Kain, et al., (1995) Bio Techniques 19:650-655 and Chiu, et al., (1996) Current Biology 6:325-330. In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate and phosphinothricin.

In some embodiments, the expression cassettes disclosed herein comprise a polynucleotide of interest encoding scorable or screenable markers, where presence of the polynucleotide produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP) and DsRed2 (Clontechniques, 2001) where plant cells transformed with the marker gene are red in color, and thus visually selectable. Additional examples include a p-lactamase gene encoding an enzyme for which various chromogenic substrates are known (e.g., PADAC, a chromogenic cephalosporin), a xylE gene encoding a catechol dioxygenase that can convert chromogenic catechols, an .alpha.-amylase gene and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as .beta.-galactosidase and fluorescent proteins such as green fluorescent protein (GFP) (Su, et al., (2004) Biotechnol Bioeng 85:610-9 and Fetter, et al., (2004) Plant Cell 16:215-28), cyan florescent protein (CYP) (Bolte, et al., (2004) J. Cell Science 117:943-54 and Kato, et al., (2002) Plant Physiol 129:913-42) and yellow florescent protein (PhiYFP™ from Evrogen, see, Bolte, et al., (2004) J. Cell Science 117:943-54). For additional selectable markers, see generally, Yarranton, (1992) Curr. Opin. Biotech. 3:506-511; Christopherson, et al., (1992) Proc. Natl. Acad. Sci. USA 89:6314-6318; Yao, et al., (1992) Cell 71:63-72; Reznikoff, (1992) Mol. Microbiol. 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc. Natl. Acad. Aci. USA 86:5400-5404; Fuerst, et al., (1989) Proc. Natl. Acad. Sci. USA 86:2549-2553; Deuschle, et al., (1990) Science 248:480-483; Gossen, (1993) Ph.D. Thesis, University of Heidelberg; Reines, et al., (1993) Proc. Natl. Acad. Sci. USA 90:1917-1921; Labow, et al., (1990) Mol. Cell. Biol. 10:3343-3356; Zambretti, et al., (1992) Proc. Natl. Acad. Sci. USA 89:3952-3956; Baim, et al., (1991) Proc. Natl. Acad. Sci. USA 88:5072-5076; Wyborski, et al., (1991) Nucleic Acids Res. 19:4647-4653; Hillenand-Wissman, (1989) Topics Mol. Struc. Biol. 10:143-162; Degenkolb, et al., (1991) Antimicrob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-919; Hlavka, et al., (1985) Handbook of Experimental Pharmacology, Vol. 78 (Springer-Verlag, Berlin); Gill, et al., (1988) Nature 334:721-724. Such disclosures are herein incorporated by reference. The above list of selectable marker genes is not meant to be limiting. Any selectable marker gene can be used in the compositions and methods disclosed herein.

Typical vectors useful for expression of genes in higher plants are well known in the art and include vectors derived from the tumor-inducing (Ti) plasmid of *Agrobacterium tumefaciens* described by Rogers, et al., (1987) Meth. Enzymol. 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) Gene 61:1-11 and Berger, et al., (1989) Proc. Natl. Acad. Sci. USA, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a "strong promoter" drives expression of a coding sequence at a "high level," or about $1/10$ transcripts to about $1/100$ transcripts to about $1/1,000$ transcripts.

In additional embodiments, enhancer elements may be introduced which increase expression of the polynucleotides of the invention.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HAS tk promoter or pgk (phosphoglycerate kinase) promoter), an enhancer (Queen, et al., (1986) Immunol. Rev. 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., 1992).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, VA, pp. 213-38 (1985)).

In addition, the S-RNAse gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert an S-RNAse polynucleotide into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) Crit. Rev. Plant Sci. 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos.

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Reducing the Activity of an S-RNAse Polypeptide

In certain embodiments the invention may include modulation of the S-RNAse gene to reduce or eliminate the activity of an S-RNAse polypeptide, perhaps during certain developmental stages or tissues etc., by transforming a plant cell with an expression cassette that expresses a polynucleotide that inhibits the expression of the S-RNAsepolypeptide, results in translation of an inactive form of S-RNAse, or deletes all or part of the S-RNAse coding sequence. The polynucleotide may inhibit the expression of the S-RNAse-polypeptide directly, by preventing transcription or translation of the S-RNAse messenger RNA, or indirectly, by encoding a polypeptide that inhibits the transcription or translation of an S-RNAse gene encoding an S-RNAsepolypeptide. Methods for inhibiting or eliminating the expression of a gene in a plant are well known in the art, and any such method may be used in the present invention to inhibit the expression of the S-RNAsepolypeptide. Many methods may be used to reduce or eliminate the activity of an S-RNAsepolypeptide. In addition, more than one method may be used to reduce the activity of a single S-RNAse-polypeptide.

1. Polynucleotide-Based Methods:

In some embodiments of the present invention, a plant is transformed with an expression cassette that is capable of expressing a polynucleotide that inhibits the expression of an S-RNAse polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one S-RNAsepolypeptide is an expression cassette capable of producing an RNA molecule that inhibits the transcription and/or translation of at least one S-RNAse polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an S-RNAse polypeptide are given below.

i. Sense Suppression/Cosuppression

In some embodiments of the invention, inhibition of the expression of an S-RNAse polypeptide may be obtained by sense suppression or cosuppression. For cosuppression, an expression cassette is designed to express an RNA molecule corresponding to all or part of a messenger RNA encoding an S-RNAse polypeptide in the "sense" orientation. Over expression of the RNA molecule can result in reduced expression of the native gene. Accordingly, multiple plant lines transformed with the cosuppression expression cassette are screened to identify those that show the greatest inhibition of S-RNAse polypeptide expression.

The polynucleotide used for cosuppression may correspond to all or part of the sequence encoding the S-RNAse polypeptide, all or part of the 5' and/or 3' untranslated region of an S-RNAse polypeptide transcript, or all or part of both the coding sequence and the untranslated regions of a transcript encoding an S-RNAse polypeptide. In some embodiments where the polynucleotide comprises all or part of the coding region for the S-RNAse polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323; herein incorporated by reference.

ii. Antisense Suppression

In some embodiments of the invention, inhibition of the expression of the S-RNAse polypeptide may be obtained by antisense suppression. For antisense suppression, the expression cassette is designed to express an RNA molecule complementary to all or part of a messenger RNA encoding the S-RNAse polypeptide. Over expression of the antisense RNA molecule can result in reduced expression of the native gene. Accordingly, multiple plant lines transformed with the antisense suppression expression cassette are screened to identify those that show the greatest inhibition S-RNAse polypeptide expression.

The polynucleotide for use in antisense suppression may correspond to all or part of the complement of the sequence encoding the S-RNAse polypeptide, all or part of the complement of the 5' and/or 3' untranslated region of the S-RNAse transcript, or all or part of the complement of both the coding sequence and the untranslated regions of a transcript encoding the S-RNAse polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

iii. Double-Stranded RNA Interference

In some embodiments of the invention, inhibition of the expression of an S-RNAse polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of S-RNAse polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of an S-RNAse polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731; and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and U.S. Patent Publication No. 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and U.S. Patent Publication No. 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the S-RNAse polypeptide). Methods of using amplicons to inhibit the expression of endogenous plant genes are described, for example, in Angell and Baulcombe, (1997) *EMBO J* 16:3675-3684, Angell and Baulcombe, (1999) *Plant J.* 20:357-362, and U.S. Pat. No. 6,635,805, each of which is herein incorporated by reference.

vi. Ribozymes

In some embodiments, the polynucleotide expressed by the expression cassette of the invention is catalytic RNA or has ribozyme activity specific for the messenger RNA of the S-RNAse polypeptide. Thus, the polynucleotide causes the degradation of the endogenous messenger RNA, resulting in reduced expression of the S-RNAse polypeptide. This method is described, for example, in U.S. Pat. No. 4,987,071, herein incorporated by reference.

vii. Small Interfering RNA or Micro RNA

In some embodiments of the invention, inhibition of the expression of S-RNAse polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of S-RNAse expression, the 22-nucleotide sequence is selected from an S-RNAse transcript sequence and contains 22 nucleotides of said S-RNAse sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding an S-RNAse polypeptide, resulting in reduced expression of the gene. In particular embodiments, the zinc finger protein binds to a regulatory region of an S-RNAse gene. In other embodiments, the zinc finger protein binds to a messenger RNA encoding an S-RNAse polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355; each of which is herein incorporated by reference.

3. Polypeptide-Based Inhibition of Protein Activity

In some embodiments of the invention, the polynucleotide encodes an antibody that binds to at least one S-RNAse polypeptide and reduces the activity of the S-RNAse polypeptide. In another embodiment, the binding of the antibody results in increased turnover of the antibody-S-RNAse complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an S-RNAse polypeptide may be reduced or eliminated by disrupting the gene encoding the S-RNAse polypeptide. The gene encoding the S-RNAse polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have desired traits.

i. Transposon Tagging

In one embodiment of the invention, transposon tagging is used to reduce or eliminate the S-RNAse activity of one or more S-RNAse polypeptides. Transposon tagging comprises inserting a transposon within an endogenous S-RNAse gene to reduce or eliminate expression of the S-RNAse polypeptide. "S-RNAse gene" is intended to mean the gene that encodes an S-RNAse polypeptide.

In this embodiment, the expression of one or more S-RNAse polypeptides is reduced or eliminated by inserting a transposon within a regulatory region or coding region of the gene encoding the S-RNAse polypeptide. A transposon that is within an exon, intron, 5' or 3' untranslated sequence, a promoter, or any other regulatory sequence of an S-RNAse gene may be used to reduce or eliminate the expression and/or activity of the encoded S-RNAse polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions in Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function of the encoded protein are well known in the art. Insertional mutations in gene exons usually result in null mutants. Mutations in conserved residues are particularly effective in inhibiting the activity of the encoded protein. Conserved residues of plant S-RNAse polypeptides suitable for mutagenesis with the goal to eliminate S-RNAse activity have been described. Such mutants can be isolated according to well-known procedures, and mutations in different S-RNAse loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more S-RNAse polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

The methods of the invention provide for improved plant performance such as stress tolerance, biomass accumulation or grain yield. This performance may be demonstrated in a number of ways including the following.

Method of Use for S-RNAse Polynucleotide, Expression Cassettes, and Additional Polynucleotides The nucleotides, expression cassettes and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,049); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,736,514; 5,723,756; 5,593,881; Geiser, et al., (1986) Gene 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

Genome Editing and Induced Mutagenesis

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein is generated using "custom" meganucleases produced to modify plant genomes (see, e.g., WO 2009/114321; Gao, et al., (2010) Plant Journal 1:176-187). Other site-directed engineering is through the use of zinc finger domain recognition coupled with the restriction properties of restriction enzyme. See, e.g., Urnov, et al., (2010) Nat Rev Genet. 11(9):636-46; Shukla, et al., (2009) Nature 459(7245):437-41.

Genome editing technologies are an alternative tool for a precise and efficient site-specific mutagenesis. Unlike conventional transformation, genome editing avoids the modification of regions other than the target sites (Bortesi and Fischer, 2015). Using double strand breaks (DSB), engineered endonucleases cut targeting DNA, triggering the response of endogenous cell repair mechanisms. Through homology directed repair (HDR) or non-homologous end joining (NHEJ) repair, broken strands are repaired, generating frame-shift mutations at the coding region and consequently, blocking or altering the expression of specific genes (Pellagatti et al., 2015; Bortesi and Fischer, 2015). Thus, the type II clustered regularly interspaced short palindromic repeat (CRISPR)-associated protein 9 (Cas9) system, emerges as practical gene editing tool, involving a guide RNAs (gRNA) constituted generally by 20 base pairs (bp), which recognizes target DNA regions (Doudna and Charpentier, 2014). This recognition, provides the substrate for the Cas9 endonuclease, through the recognition a protoespacer-adjacent motif (PAM), a three bp sequence (5'-NGG and 5'-NAG for CRISP/Cas9), facilitating the transition between target recognition and cleavage, ending up in the generation of a DSB (Doudna and Charpentier, 2014; Pellagatti et al., 2015; Sternberg et al., 2014).

In one embodiment, the disclosure relates to a plant with reduced expression of an S-RNAse gene and/or reduced activity of the S-RNAse protein, wherein reduced expression of the S-RNAse gene and/or reduced activity of the S-RNAse protein is achieved by genomic editing.

Genome editing, or genome editing with engineered nucleases (GEEN), is a type of genetic engineering in which DNA is inserted, replaced, or removed from a genome using artificially engineered nucleases, or "molecular scissors." The nucleases create specific double-stranded breaks (DSBs) at desired locations in the genome and harness the cell's endogenous mechanisms to repair the induced break by natural processes of homologous recombination (HR) and nonhomologous end-joining (NHEJ). There are currently four main families of engineered nucleases being used: Zinc finger nucleases (ZFNs), Transcription Activator-Like Effector Nucleases (TALENs), the CRISPR/Cas system, and engineered meganuclease with a re-engineered homing endonuclease.

A. Zinc Finger Nucleases (ZFNs)

Zinc-finger nucleases (ZFNs) are artificial restriction enzymes generated by fusing a zinc finger DNA-binding domain to a DNA-cleavage domain. Zinc finger domains can be engineered to target specific desired DNA sequences, and this enables zinc-finger nucleases to target unique sequences within complex genomes. By taking advantage of endogenous DNA repair machinery, these reagents can be used to precisely alter the genomes of higher organisms.

ZFNs consist of an engineered zinc finger DNA-binding domain fused to the cleavage domain of the FokI restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome.

Publicly available methods for engineering zinc finger domains include: (1) Context-dependent Assembly (CoDA), (2) Oligomerized Pool Engineering (OPEN), and (3) Modular Assembly.

In one embodiment, the disclosure relates to reducing expression of the S-RNAse gene and/or reducing activity of the S-RNAse protein using ZFNs.

B. Transcription Activator-Like Effector Nucleases (TALENs)

TALEN is a sequence-specific endonuclease that consists of a transcription activator-like effector (TALE) and a FokI endonuclease. TALE is a DNA-binding protein to that has a highly conserved central region with tandem repeat units of 34 amino acids. The base preference for each repeat unit is determined by two amino acid residues called the repeat-variable di-residue (RVD), which recognizes one specific nucleotide in the target DNA. Arrays of DNA-binding repeat units can be customized for targeting specific DNA sequences. As with ZFNs, dimerization of two TALENs on targeted specific sequences in a genome results in FokI-dependent introduction of DSBs, stimulating homology directed repair (HDR) and Non-homologous end joining (NHEJ) repair mechanisms.

In one embodiment, the disclosure relates to reducing expression of the S-RNAse gene and/or reducing activity of the S-RNAse protein using TALENs.

C. CRISPR/Cas System

The Clustered Regularly Interspaced Short Palindromic Repeats (CRISPR) Type II system is an RNA-Guided Endonuclease technology for genome engineering. There are two distinct components to this system: (1) a guide RNA and (2) an endonuclease, in this case the CRISPR associated (Cas) nuclease, Cas9.

The guide RNA is a combination of the endogenous bacterial crRNA and tracrRNA into a single chimeric guide RNA (gRNA) transcript. The gRNA combines the targeting specificity of the crRNA with the scaffolding properties of the tracrRNA into a single transcript. When the gRNA and the Cas9 are expressed in the cell, the genomic target sequence can be modified or permanently disrupted.

The gRNA/Cas9 complex is recruited to the target sequence by the base-pairing between the gRNA sequence and the complementarity to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 3-4 nucleotides upstream of the PAM sequence. A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene.

The HDR pathway requires the presence of a repair template, which is used to fix the DSB. HDR faithfully copies the sequence of the repair template to the cut target sequence. Specific nucleotide changes can be introduced into a targeted gene by the use of HDR with a repair template.

In one embodiment, the disclosure relates to reducing expression of the S-RNAse gene and/or reducing activity of the S-RNAse protein using the CRISPR/cas9 system or similar technology (or a variant of the technology).

D. Meganuclease with Re-Engineered Homing Nuclease

Meganucleases are endodeoxyribonucleases characterized by a large recognition site (double-stranded DNA sequences of 12 to 40 base pairs); as a result, this site generally occurs only once in any given genome. For example, the 18-base pair sequence recognized by the I-SeeI meganuclease would on average require a genome twenty times the size of the human genome to be found once by chance (although sequences with a single mismatch occur about three times per human-sized genome). Meganucleases are therefore considered to be the most specific naturally occurring restriction enzymes.

Among meganucleases, the LAGLIDADG family of homing endonucleases has become a valuable tool for the study of genomes and genome engineering over the past fifteen years. By modifying their recognition sequence through protein engineering, the targeted sequence can be changed.

In one embodiment, the disclosure relates to reducing expression of the S-RNAse gene and/or reducing activity of the S-RNAse protein using a meganuclease with a re-engineered homing nuclease "TILLING" or "Targeting Induced Local Lesions IN Genomics" refers to a mutagenesis technology useful to generate and/or identify and to eventually isolate mutagenised variants of a particular nucleic acid with modulated expression and/or activity (McCallum, et al., (2000), Plant Physiology 123:439-442; McCallum, et al., (2000) Nature Biotechnology 18:455-457 and Colbert, et al., (2001) Plant Physiology 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

TILLING also allows selection of plants carrying mutant variants. These mutant variants may exhibit modified expression, either in strength or in location or in timing (if the mutations affect the promoter, for example). These mutant variants may exhibit higher or lower activity than that exhibited by the gene in its natural form. TILLING combines high-density mutagenesis with high-throughput screening methods. The steps typically followed in TILLING are: (a) EMS mutagenesis (Redei and Koncz, (1992) In Methods in Arabidopsis Research, Koncz, et al., eds. Singapore, World Scientific Publishing Co, pp. 16-82; Feldmann, et al., (1994) In Arabidopsis. Meyerowitz and Somerville, eds, Cold Spring Harbor Laboratory Press, Cold Spring Harbor, N.Y., pp 137-172; Lightner and Caspar, (1998) In Methods on Molecular Biology 82:91-104; Martinez-Zapater and Salinas, eds, Humana Press, Totowa, N.J.); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (U.S. Pat. No. 8,071,840).

Other mutagenic methods can also be employed to introduce mutations in a disclosed gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Embodiments of the disclosure reflect the determination that the genotype of an organism can be modified to contain dominant suppressor alleles or transgene constructs that suppress (i.e., reduce, but not ablate) the activity of a gene, wherein the phenotype of the organism is not substantially affected.

Hybrid Seed Production

Hybrid seed production requires elimination or inactivation of pollen produced by the female parent. Incomplete removal or inactivation of the pollen provides the potential for selfing, raising the risk that inadvertently self-pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor relative to the hybrid plants. For example, female selfed plants of e are identified by their less vigorous appearance for vegetative and/or reproductive characteristics, including shorter plant height, small ear size, ear and kernel shape, cob color or other characteristics. Selfed lines also can be identified using molecular marker analyses (see, e.g., Smith and Wych, (1995) Seed Sci. Technol. 14:1-8). Using such methods, the homozygosity of the self-pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. A large number of genes have been identified as being pollen preferred in their expression pattern using traditional methods and more recent high-throughput methods. The correlation of function of these genes with important biochemical or developmental processes that ultimately lead to functional pollen is arduous when approaches are limited to classical forward or reverse genetic mutational analysis. As disclosed herein, suppression approaches provide an alternative rapid means to identify genes that are directly related to pollen development.

Potato exists in different ploidy levels (di-, tri-, tetra-, penta-, and hexa-ploid), and for development of hybrids it is preferred to work on a diploid level because homozygous lines are much faster obtained at the diploid level than at the tetraploid level. And in addition, complex traits are much more efficient to breed for at the diploid level. After a homozygous diploid is made, it may be beneficial to increase ploidy back to tetraploid, e.g., through treatment with cylcohiximide. Polyploid plants often show increased vigor vs. diploids.

Use in Breeding Methods

The transformed plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity and plant are desirable. Traditional plant breeding is an important tool in developing new and improved commercial crops. This disclosure encompasses methods for producing a plant by crossing a first parent plant with a second parent plant wherein one or both of the parent plants is a transformed plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed plant to an elite inbred line and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Overcoming Self-Incompatibility in Diploid Potato Using Genome Editing

Potato breeding programs rely on the discovery and introgression of genes of interest. However, the polyploid nature of potatoes hampers the fixation of desirable alleles in new cultivars. Therefore, creating inbred diploid potatoes represents an alternative strategy for obtaining homozygous lines. However, diploid potatoes possess self-incompatibility (SI) that forces outcrossing and limits potato inbred line development. In the gametophytic self-incompatibility system, characteristic of the Solanaceae family, the S-locus F-box protein expressed in the pollen does not recognize its own S haplotype of the style (S-RNAse), expressed in the pistil, inhibiting the elongation of self-pollen tubes by degrading RNA. The aim of this project is to generate a targeted knock-out of the S-RNase locus in self-incompatibility potato lines using Clustered Regularly Interspaced Short Palindromic Repeats/CRISPR-associated systems (CRISPR/Cas9) technology in an effort to avoid self-pollen toxicity. Three diploid self-incompatible lines (DHR-195, DRH-310 and MSX914-10 respectively) from the Michigan State University potato breeding program are being used. Seven reported S-RNAse genes in Solanaceae species were selected according to their functional evidence in self-incompatibility mechanism. These sequences were aligned against the lines/parental genomes and resulting orthologs were compared with expression data sets to identify functional homologues on each line. Structural annotation of the candidate gene revealed two exons and one intron and gRNAs were designed from conserved regions and assembled in an expression vector carrying the Cas9, U6 promoter and scaffold guide RNA that were inserted into the T-DNA region of *Agrobacterium tumefaciens* and used in transformation. One out of 2 different expression vectors was selected for its targeting efficiency, via PEG-mediated transformation. To date, 20 and 4 transformation events for DRH-195 and DRH-310 respectively, have been selected for InDel presence and confirmed by sequencing. The S-RNase knock out mutants will be verified for self-compatibility in greenhouse and grow chamber and differential expression by real time PCR.

As a staple food, the potato (*Solanum tuberosum* L.), plays an important role in human nutrition. It is considered a main source of carbohydrates, providing the energy needed for human development and function. Along with beans, potato is considered as the cheapest source of fiber, minerals, and vitamins (Drewnowski and Rehm, 2013). Additionally, potatoes possess a high content of phenolic compounds, opening a new window for potato's commercialization as a functional food due to its potential antioxidant activity (Friedman, 1997; Vinson et al., 2012). Currently, the potato is considered one of most important agricultural commodity reaching a total global production of 376 million tons in 2016 (FAOSTAT, 2018). However, this tuber faces high production losses caused mainly by biotic and abiotic factors, with an increasingly negative impact on potato yield, boosted by global warming (Raymundo et al., 2017).

Potato breeding programs rely on the discovery and introgression of genes of interest for traits such as disease resistance from wild species into cultivated potatoes. However, the polyploid nature of potatoes hampers the fixation of desirable alleles in new cultivars. For example, important recessive alleles such as the virus Y disease resistant gene (Ruffel et al., 2002), are difficult to fix in breeding populations, due to their recessive nature (hidden in simplex, duplex or triplex configurations), making difficult the generation of homogeneous lines for the traits of interest. Therefore, creating inbred diploid potatoes represents one alternative for obtaining breeding lines with homozygous loci, enhancing genetic gains by exploiting the additive gene action. Inbred potatoes will accelerate the generation of new varieties with favorable allele combinations, targeting yield, tuber quality, and resistant traits. Furthermore, diploid cultivated potatoes will enable the implementation of genetic approaches developed in diploid species to understand the genetic basis of most important agronomic traits (Jansky et al., 2016).

However, diploid potatoes possess self-incompatible (SI) mechanisms that prevent inbreeding. Specifically, in potatoes, the gametophytic self-incompatibility system is controlled by a single multiallelic locus called the S locus (Porcher and Lande, 2005). This locus is composed of two tightly linked genes, the S-locus F-box protein (SLF), and style-specific ribonucleases (S-RNAses), expressed in pollen and the style, respectively (Takayama and Isogai, 2005). The SLF protein functions as a component of a detoxification complex that mediates ubiquitination of target proteins for degradation via proteasome pathway. In this case, the target protein is a non-self S-RNAse (Kubo et al., 2015). On the other hand, the S-RNAse protein produces cytotoxic effects that inhibit the elongation of self-pollen tubes by degrading RNA from the pollen (Kubo et al., 2015). Hence, when self-pollination occurs, SLF does not recognize its own S-RNAse and consequently, this lack of recognition results in the inhibition of pollen tube growth in the style (Ai et al., 1992).

In this sense, self-incompatibility represents a limitation for diploid potato breeding, preventing the ability to cross selected parental lines and make backcrosses in the presence of the same S alleles (Abdalla and Hermsen, 1972). As an effort to develop diploid-self-compatible potato lines, the highly inbred line M6, from the close related species *Solanum chacoense*, has been generated (Jansky et al., 2014), using the S locus inhibitor (Sli), discovered in the same species (Hosaka and Hanneman, 1998). However, this process can be time-consuming and could lead to the fixation of undesirable traits such as glycoalkaloids through linkage drag. Therefore, the use of cutting-edge technologies such as genome editing to accelerate the generation of self-compatible diploid lines by targeting the genes involved in self-incompatibility.

Genome editing technologies arise as an alternative tool for a precise and efficient site-specific mutagenesis. Unlike conventional transformation, genome editing avoids the modification of regions other than the target sites (Bortesi and Fischer, 2015). Using double strand breaks (DSB), engineered endonucleases cut targeting DNA, triggering the response of endogenous cell repair mechanisms. Through homology directed repair (HDR) or non-homologous end joining (NHEJ) repair, broken strands are repaired, generating frame-shift mutations at the coding region and consequently, blocking or altering the expression of specific genes (Pellagatti et al., 2015; Bortesi and Fischer, 2015). Thus, the type II clustered regularly interspaced short palindromic repeat (CRISPR)-associated protein 9 (Cas9) system, emerges as practical gene editing tool, involving a guide RNAs (gRNA) constituted generally by 20 base pairs (bp), which recognizes target DNA regions (Doudna and Charpentier, 2014). This recognition, provides the substrate for the Cas9 endonuclease, through the recognition a protoespacer-adjacent motif (PAM), a three bp sequence (5'-NGG and 5'-NAG for CRISP/Cas9), facilitating the transition between target recognition and cleavage, ending up in the generation of a DSB (Doudna and Charpentier, 2014; Pellagatti et al., 2015; Sternberg et al., 2014).

To contribute to the generation of diploid inbred potato lines the present project seeks to generate a targeted knock-out of the S-RNase gene in self-incompatibility potato lines using CRISPR-associated Cas9 technology in an effort to avoid self-pollen toxicity.

Materials and Methods

Plant Material

Two diploid potato lines (2n=2x=24) generated at VirginiaTech and Michigan State University potato breeding programs were used for this study. The DRH-195 and DRH-310 F1 lines were derived from a cross between the double monoploid (DM) DM 1-3 516 R44 *S. tuberosum* group Phureja (DM 1-3) and heterozygous breeding line RH 89-039-16 *S. tuberosum* group *Tuberosum*. Similarly, the MSX914-10 line generated from the cross of DM and the 84SD22 (with a *S. chacoense* and *S. tuberosum* pedigree). Plants were maintained in in-vitro conditions for further experiments.

S-RNAse Homolog Identification and Annotation

To identify the S-RNAse homolog in diploid potatoes we first generated genome assemblies for the DRH-195 and DRH-310 lines. Genomic and RNA sequence data from DRH-195 and DRH-310 leaf and tuber tissues were retrieved from the Sequence Read Archive (SRA) of the National Center for Biotechnology Information (Table A).

TABLE A

| | DMRH-195 | | DMRH-310 | |
|---|---|---|---|---|
| Tissue | SRA acc. | Reads | SRA acc. | Reads |
| Leaflet | | 61.598.468 | | 49.783.826 |
| | SRX2011949 | 30,799,234 | SRX2011955 | 24,891,913 |
| Leaf | SRX2011905 | 30.423.428 | SRX2011911 | 29.113.282 |
| Tuber | SRX2011928 | 31.800.294 | SRX2011932 | 31.283.414 |
| Total: | | 123.822.190 | | 110.180.522 |
| Genome coverage: | | 9.37X | | 2.64X |

Combined reads for each DRH line were assembled by mapping them in the DM v3.04 potato genome assembly (Hardigan et al., 2016) using BWA v0.7.12 (Li and Durbin, 2009). Duplicate reads were removed using Picard Tools v1.113 (world wide web at broadinstitute.github.io/picard), re-aligning the remaining reads with GATK v3.4.46 (McKenna et al., 2010). Finally, the genome assemblies were obtained using the mpileup utility from Samtools v1.2 (Li et al., 2009) and the consensus option from bcftools v1.2 TBLASTN and BLASTN (BLAST-basic local alignment search tool) searches were performed using reported S-RNAse genes or proteins from the Solanaceae family (selected according to their functional evidence) against the DM (Hardigan et al., 2016), M6 (Leisner et al., 2018) and DRH-195/310 assemblies using BLAST v2.2.31 (Altschul et al., 1990) with default parameters. The top blast hit for each gene was used to select a genomic region on each assembly. Similarly, homolog CDS and protein sequences were selected from the best blast hit against the DM CDS and proteome datasets (The Potato Genome Sequencing Consortium, 2011) using BLASTN and BLASTP respectively.

Selected genomic, CDS and protein sequences were used to predict the S-RNAse gene structure of the three diploid potato lines using MAKER v2.31.10 (Cantarel et al., 2008) with default parameters. Additionally, a tissue-specific expression pattern associated with the selected S-RNAse homolog was obtained comparing the top CDS and proteome blast hits for DM and M6 genomes with available RNAseq datasets for these two lines (world wide web at solanaceae.plantbiology.msu.edu/pgsc_download.shtml).

S-RNAse Mapping

The S-RNAs locus was mapped in the diploid mapping population DRH, a pseudo-test cross between DM 1-3 and RH. The S-RNAse allele specific sequences of DM 1-3 and RH parents were used to generate a marker to screen the population and map into the DRH genetic map reported by Manrique-Carpintero et al. (2015). A set of primers was designed to amplify the predicted open reading frame (ORF) of the S-RNAse locus (F-ATGTTTAAATCACTGCTTACATCAAC (SEQ IDNO:57) and R-TCAGGGACG-GAAAAATATTTTCCCTG) (SEQ ID NO:58) in DRH-195 and DRH-310, each with different S-RNAse allele inherited from RH parent based on phase information of genetic map. DNA was isolated from young leaves using the DNeasy Plant Mini Kit (Qiagen), and used for polymerase chain reaction (PCR) with a Q5® High-Fidelity DNA Polymerase (BioLabs) with the following thermocycler conditions: one cycle of initial denaturation for 4 min at 94° C., followed by 34 cycles for 15 s at 94° C., 45 s at 56° C. and 1 min at 72° C. and a final extension of 5 min at 72° C. Amplicons were gel-purified using the QIAquick PCR Purification Kit (Qiagen) and cloned into TOPO PCR Cloning vector (ThermoFisher). Ten colonies for each line were sequenced by the Sanger method and aligned using Clustal Omega (Sievers et al., 2011). DM 1-3 and RH allelic sequences were confirmed and used to design allele-specific primers of S-RNase to screen 82 individuals of the mapping population. The presence/absence of an RH allele was used for genotyping, the genotypes coded as nnxnp and used for mapping in JoinMap4.1 using same parameter as reported by Manrique-Carpintero et al. (2015), gRNA Identification, Assembly and Validation Three gRNAs targeting conserved regions within both exons of the predicted S-RNAse homologs were designed using Cas-Designer from CRISPR RGEN tools (Park et al., 2015). Gene knockout constructs containing two gRNAs combinations (gRNA1-3 and gRNA2-3) were assembled using the pHSE40 vector containing the CRISPR-Cas9 cassette as described by Xing et al. (2014). Each assembled construct was transformed into *Agrobacterium tumefaciens* strain GV3101 by electroporation and stored in 80% glycerol at −80° C. until use.

*Agrobacterium*-Mediated Transformation

*Agrobacterium*-mediated transformation was performed using four weeks-old stem (MSX914-10) and leaf (DRH 195 and DRH 310) explants as described by (Li et al., 1999) with some modifications: transformation events were selected from callus induction medium containing 20 mgL hygromycin and 150 mgL timentin for MSX914-10 and an additional 250 mgL cefotaxime for DRH-195 and DRH-310. Selected plants were transferred to root induction media containing the first two antibiotics for all lines.

InDel Detection, Cloning and Sequencing

DNA from transformation events was isolated as described here in. PCR's were carry out using the GoTaq DNA polymerase (Promega) with the following thermocycler conditions: one cycle of initial denaturation for 4 min at 94° C., followed by 34 cycles for 15 s at 94° C., 45 s at 55° C. and 1 min at 72° C. and a final extension of 5 min at 72° C. Amplicons were visualized on 1% (w/v) agarose gels. Selected transformation events were PCR-amplified using the Q5 High-Fidelity DNA Polymerase (BioLabs) following manufacturer's instructions. Purified PCR products were cloned into the TOPO TA vector (ThermoFisher) and transformed into DH5alpha competent cells (Thermofisher). Colonies carrying the alleles from each event were sequenced by Sanger at the MSU sequencing facility.

Self-Pollination Experiment

One month old in-vitro plants were planted in one gallon plastic pots with a peat and perlite grown medium mixture and placed into a grow chamber with a light intensity of 250 mE m$^{-2}$ s$^{-1}$, 16/8-h light/dark photoperiod and a temperature of 25° C. Plants were fertilized with Peters 20:20:20 fertilizer (1 gr/l) once a week. A minimum of 20 flowers per plants were self-pollinated by hand.

References

Abdalla, M. and Hermsen, J. (1972) *Unilateral incompatibility: hypotheses, debate and its implications for plant breeding. Euphytica*, 21, 32-47.

Ai, Y., Singh, A., Coleman, C. E., Ioerger, T. R., and Kheyr-pour, A. (1990) *Self-incompatibility in Petunia inflata: isolation and characterization of cDNAs encoding three S-allele-associated proteins. Sexual Plant Reproduction*, 3, 130-138.

Ai, Y., Tsai, D., and Kao, T. (1992) *Cloning and sequencing of cDNAs encoding two S proteins of a self-compatible cultivar of Petunia hybrida*. 81685, 523-528.

Altschul, S. F., Gish, W., Miller, W., Myers, E. W., and Lipman, D. J. (1990) *Basic Local Alignment Search Tool. J. Mol. Biol*, 215, 403-410.

Bortesi, L. and Fischer, R. (2015) *The CRISPR/Cas9 system for plant genome editing and beyond. Biotechnology Advances*, 33, 41-52.

Cantarel, B. L., Korf, I., Robb, S. M. C., Parra, G., Ross, E., Moore, B., et al. (2008) *MAKER: An easy-to-use annotation pipeline designed for emerging model organism genomes. Genome Research*, 18, 188-196.

Doudna, J. A. and Charpentier, E. (2014) *The new frontier of genome engineering with CRISPR-Cas9. Science*, 346, 1258096-1258096.

Drewnowski, A. and Rehm, C. D. (2013) *Vegetable Cost Metrics Show That Potatoes and Beans Provide Most Nutrients Per Penny. PLoS ONE*, 8, e63277.

FAOSTAT (2018) *FAOSTAT database collections. Food and Agriculture Organization of the United Nations.*

Friedman, M. (1997) *Chemistry, Biochemistry, and Dietary Role of Potato Polyphenols: A Review. Journal of Agricultural and Food Chemistry*, 45, 1523-1540.

Golz, J. F., Clarke, A. E., Newbigin, E., and Anderson, M. (1998) *A relic S-RNase is expressed in the styles of self-compatible Nicotiana sylvestris.* 16, 591-599.

Hardigan, M. A., Crisovan, E., Hamiltion, J. P., Kim, J., Laimbeer, P., Leisner, C. P., et al. (2016) *Genome reduction uncovers a large dispensable genome and adaptive role for copy number variation in asexually propagated Solanum tuberosum. The Plant Cell*, 28, 388-405.

Hosaka, K. and Hanneman, R. E. (1998) *Genetics of self-compatibility in a self-incompatible wild diploid potato species Solanum chacoense. 1. Detection of an S locus inhibitor (Sli) gene. Euphytica*, 99, 191-197.

Jansky, S. H., Charkowski, A. O., Douches, D. S., Gusmini, G., Richael, C., Bethke, P. C., et al. (2016) *Reinventing Potato as a Diploid Inbred Line—Based Crop. Crop Science*, 56, 1412-1422.

Jansky, S. H., Chung, Y. S., and Kittipadukal, P. (2014) *M6: A diploid potato inbred line for use in breeding and genetics research. Journal of Plant Registrations*, 8, 195-199.

Kaufmann, H., Salamini, F., and Thompson, R. D. (1991) *Sequence variability and gene structure at the self-incompatibility locus of Solanum tuberosum.*

Kondo, K., Yamamoto, M., Itahashi, R., Sato, T., Egashira, H., and Hattori, T. (2002) *Insights into the evolution of self-compatibility in Lycopersicon from a study of stylar factors.* 30.

Kubo, K., Paape, T., Hatakeyama, M., Entani, T., Takara, A., Kajihara, K., et al. (2015) *Gene duplication and genetic exchange drive the evolution of S-RNase-based self-incompatibility in Petunia. Nature Plants*, 1, 14005.

Leisner, C. P., Hamilton, J. P., Crisovan, E., Manrique-Carpintero, N. C., Marand, A. P., Newton, L., et al. (2018) *Genome sequence of M6, a diploid inbred clone of the high-glycoalkaloid-producing tuber-bearing potato species Solanum chacoense, reveals residual heterozygosity. The Plant Journal*, 94, 562-570.

Li, H. and Durbin, R. (2009) *Fast and accurate short read alignment with Burrows-Wheeler transform. Bioinformatics* (Oxford, England), 25, 1754-60.

Li, H., Handsaker, B., Wysoker, A., Fennell, T., Ruan, J., Homer, N., et al. (2009) *The Sequence Alignment/Map format and SAMtools. Bioinformatics*, 25, 2078-2079.

Li, W., Zarka, K. A., Douches, D. S., Coombs, J. J., Pett, W. L., and Grafius, E. J. (1999) *Coexpression of Potato PVYo Coat Protein and cryV-Bt Genes in Potato. J. Amer. Soc. Hort. Sci*, 124, 218-223.

Manrique-Carpintero, N. C., Coombs, J. J., Cui, Y., Veilleux, R. E., Buell, C. R., and Douches, D. (2015) *Genetic Map and QTL Analysis of Agronomic Traits in a Diploid Potato Population using Single Nucleotide Polymorphism Markers. Crop Science*, 55, 2566-2579.

McKenna, A., Hanna, M., Banks, E., Sivachenko, A., Cibulskis, K., Kernytsky, A., et al. (2010) *The Genome Analysis Toolkit: A MapReduce framework for analyzing next-generation DNA sequencing data. Genome Research*, 20, 1297-1303.

Park, J., Bae, S., and Kim, J. (2015) *Sequence analysis Cas-Designer: A web-based tool for choice of CRISPR-Cas9 target sites. Bioinformatics*, 1-3.

Pellagatti, A., Dolatshad, H., Valletta, S., and Boultwood, J. (2015) *Application of CRISPR/Cas9 genome editing to the study and treatment of disease. Archives of Toxicology*, 1023-1034.

Porcher, E. and Lande, R. (2005) *LOSS OF GAMETOPHYTIC SELF-INCOMPATIBILITY WITH EVOLUTION OF INBREEDING DEPRESSION Author (s): Emmanuelle Porcher and Russell Lande LOSS OF GAMETOPHYTIC SELF-INCOMPATIBILITY WITH EVOLUTION OF. Evolution*, 59, 46-60.

Raymundo, R., Asseng, S., Robertson, R., Petsakos, A., Hoogenboom, G., Quiroz, R., et al. (2017) *Climate change impact on global potato production. European Journal of Agronomy.*

Ruffel, S., Dussault, M., Palloix, A., Moury, B., Bendahmane, A., Robaglia, C., and Caranta, C. (2002) *A natural recessive resistance gene against potato virus Yin pepper corresponds to the eukaryotic initiation factor. The Plant Journal*, 32, 1067-1075.

Saba-e-leil, M. K., Rivard, S., Morse, D., and Cappadocia, M. (1994) *The S11 and S13 self incompatibility alleles in Solanum chacoense Bitt are remarkably similar. Plant Molecular Biology*, 24, 571-583.

Sievers, F., Wilm, A., Dineen, D., Gibson, T. J., Karplus, K., Li, W., et al. (2011) *Fast, scalable generation of high-quality protein multiple sequence alignments using Clustal Omega. Molecular systems biology*, 7, 539.

Sternberg, S. H., Redding, S., Jinek, M., Greene, E. C., and Doudna, J. A. (2014) *DNA interrogation by the CRISPR RNA-guided endonuclease Cas9. Nature*, 507, 62-7.

Takayama, S. and Isogai, A. (2005) *Self-Incompatibility in Plants. Annual Review of Plant Biology*, 56, 467-489.

The Potato Genome Sequencing Consortium (2011) *Genome sequence and analysis of the tuber crop potato. Nature*, 475, 189-195.

Vinson, J. a., Demkosky, C. a., Navarre, D. a., and Smyda, M. a. (2012) *High-antioxidant potatoes: Acute in vivo antioxidant source and hypotensive agent in humans after supplementation to hypertensive subjects. Journal of Agricultural and Food Chemistry*, 60, 6749-6754.

Xing, H.-L., Dong, L., Wang, Z.-P., Zhang, H.-Y., Han, C.-Y., Liu, B., et al. (2014) *A CRISPR/Cas9 toolkit for multiplex genome editing in plants. BMC plant biology*, 14, 327.

TABLE 1

Reported SI genes/proteins in seven different species from the Solanaceae family

| Gene/protein | Avail. information | NCBI accession | Species | Experimental evidence | Reference |
| --- | --- | --- | --- | --- | --- |
| Ribonuclease S-2 | Protein | Q01796 | *Solatium tuberosum* | Probes designed from a S-RNAse protein (*N. alata*) were used to detect transcripts from pistils (4 development stages) and genomic DNA | Kaufmann et al. (1991) |

TABLE 1-continued

Reported SI genes/proteins in seven different species from the Solanaceae family

| Gene/protein | Avail. information | NCBI accession | Species | Experimental evidence | Reference |
|---|---|---|---|---|---|
| Sx-protein | Protein/CDS | AAA33729 | *Petunia x hybrida* | (BACs). Protein detection in pistil development using inmuno-detection. Stylar cDNA isolation using probes designed from reported S-RNAse proteins. Ribonuclease activity of detected alleles tested using activity-stained gel | Ai et al. (1992) |
| S11 | Protein/ Nucleotide* | AAA50306 | *Solanum chacoense* | Genome library hybridization using a reported S-RNAse alleles. Confirmation using haploid and double haploids crosses and RNA analysis from the style. | Saba-e-leil et al. (1994) |
| S-RNase | Protein/CDS | BAC00940 | *Solanum neorickii* | Confirmation of S-RNAse activity of stylar proteins. S-RNAse PCR fragments used as probes for cDNA isolation using style libraries | Kondo et al. (2002) |
| S2 self-incompatibility ribonuclease precursor | Protein/CDS | AAG21384 | *Petunia integrifolia* subsp. *inflata* | Protein sequencing (N terminal region) from pistils extracts. cDNA identification using probes designed from reported S-RNAses | Ai et al. (1990) |
| RNase | Protein/mRNA | CAA05306 | *Nicotiana sylvestris* | Protein ribonuclease activity confirmation using spectrophotometric assays. cDNA cloning from stylar RNA and temporal and spatial expression in the style. Detection of different S-RNAse alleles using southern blot | Golz et al. (1998) |
| S1-RNase | Protein/CDS | BAC00934 | *Solatium chilense* | Confirmation of S-RNAse activity of stylar proteins. S-RNAse PCR fragments used as probes for cDNA isolation using style libraries | Kondo et al. (2002) |

*Complete gene sequence

Example 2

Diploid potatoes possess self-incompatibilty (SI) loci that forces outcrossing and limits potato inbred line development. The SI system in the Solanaceae is controlled by the S-locus (SLF and S-RNAse). An F-box protein (SLF) expressed in the pollen does not recognize its own S haplotype of the style (S-RNAse) which is expressed in the pistil. The S-RNAse produces cytotoxic effects that inhibit the elongation of self-pollen tubes by degrading RNA (Takayama et al., 2015).

To generate a targeted knock-out of the S-RNAse gene in SI diploid potato lines using Clustered Regularly Interspaced Short Palindromic Repeats/CRISPRassociated systems (CRISPR/Cas9) technology in an effort to avoid self-pollen toxicity Plant material: The diploid self-incompatible lines DRH-195, DRH-310 and MSX914-10, were selected to generate the S-RNAse knock out lines Candidate S-RNAse identification and mapping: Selected S-RNAse genes (Table 1) were aligned to the *S. tuberosum* (DM 1-3) and *S. chacoense* (M6) genomes to identify S-RNAse candidate alleles.

TABLE 1

S-RNAse reported genes in Solanaceae. PMID: Pubmed ID.

| Gene/protein | Avail. information | NCBI accession | Species | Reference (PMID) |
|---|---|---|---|---|
| Ribonuclease S-2 | Protein | Q01796 | Solanum tuberosum | 2038308 |
| Sx-protein | Protein/CDS | AAA33729 | Petunia × hybrida | 1344883 |
| S11 | Protein/Nucleotide | AAA50306 | Solanum chacoense | 8155878 |
| S-RNase | Protein/CDS | BAC00940 | Solanum neorickii | 12000451 |
| S2 self-incompatibility ribonuclease precursor | Protein/CDS | AAG21384 | Petunia integrifolia subsp. inflata | Ai et al. (1990) |
| RNase | Protein/mRNA | CAA05306 | Nicotiana sylvestris | 10036777 |
| S1-RNase | Protein/CDS | BAC00934 | Solanum chilense | 12000451 |

Figure 2A:
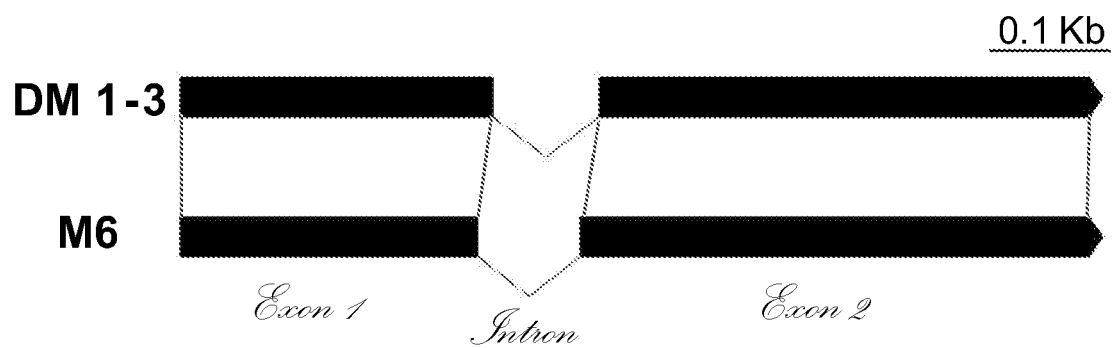
FIG. 2. A. S-RNAse architecture in DM 1-3 (738 bp) and M6 (725 bp). B. S-RNase predicted amino-acid alignment of DM 1-3, M6 and RH-derived alleles from DRH lines SQ ID NOS 22-25.
Figure 2B:

Resulting orthologs were compared with expression data sets and subjected to structural annotation. An RH-allele specific marker was developed and mapped in the previously reported DRH F1 population (Manrique-Carpintero et al., 2015). S-RNAse candidate gene knock out: Guide-RNAs were designed from conserved exonic regions of the SRNAse alleles, assembled into a vector carrying the CRISPR/Cas9 cassette (pHSE401), and used for *Agrobacterium tumefaciens*-mediated transformation (FIG. 1). Selected S-RNAse genes from the Solanaceae family. Seven S-RNAse genes from potato and other Solanaceae species were selected according to their functional evidence in SI mechanism (Table 1). S-RNAse functional and structural annotation. S-RNAse alleles in DM 1-3 and M6 genome assemblies uncovered a candidate gene with 2 exons and 1 intron expressed in flowers. From the DRH assemblies, we identified 2 RH-derived S-RNAse alleles (FIG. 2, Table 2).

TABLE 2

S-RNase ortholog position and predicted function on DM 1-3 and M6

| Species | TBLASNT | Tissue | Predicted function |
|---|---|---|---|
| DM 1-3 | Chromosome 0 | Whole mature flowers; Carpels | S protein |
| M6 | scaffold_61 | Open flowers | Ribonuclease |

Figure 3A:
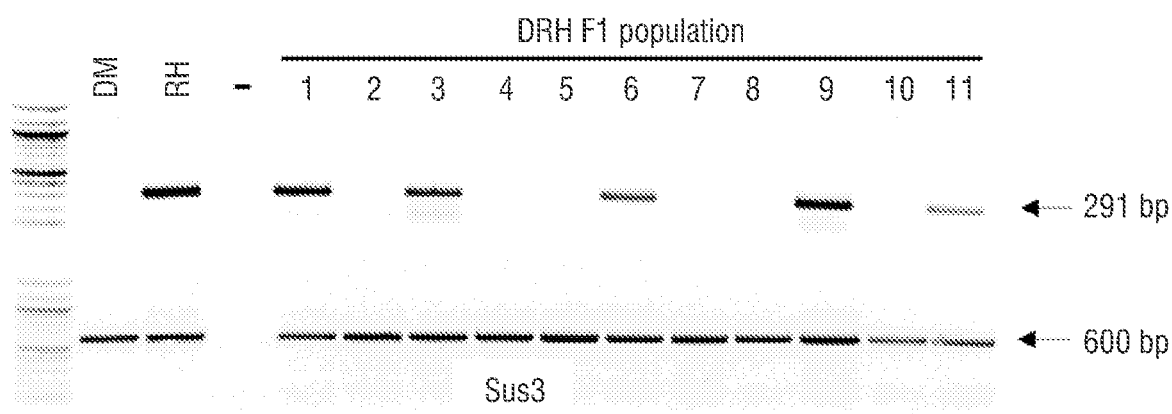
FIG. 3. A. S-RNAse screening on the DRH F1-derived population. B. S-RNase position at chromosome 1. C. Physical versus Genetic distances from chromosome 1 showing the S-RNase ortholog within a low-recombination region (box).
Figure 3B:
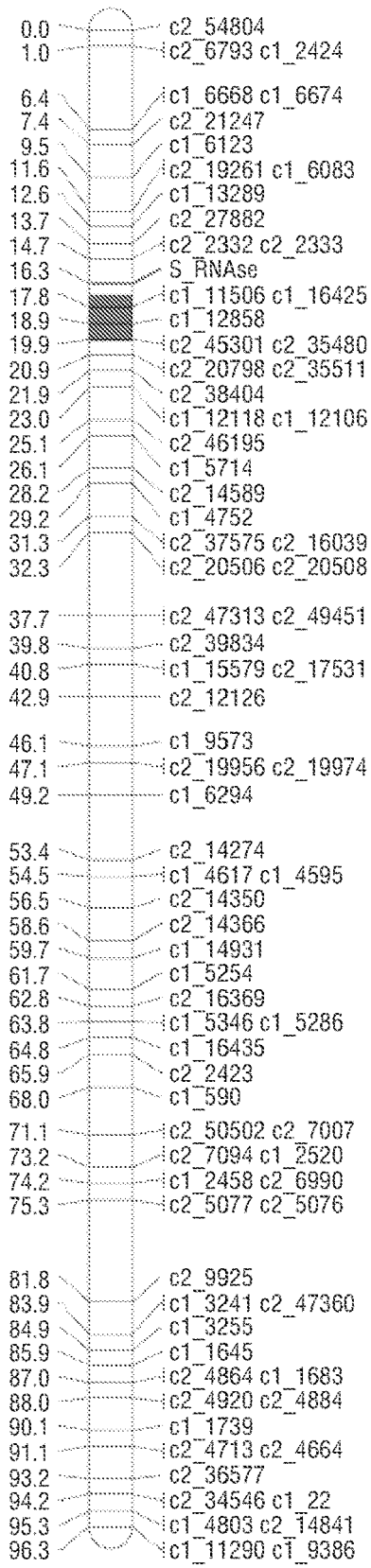
Figure 3C:
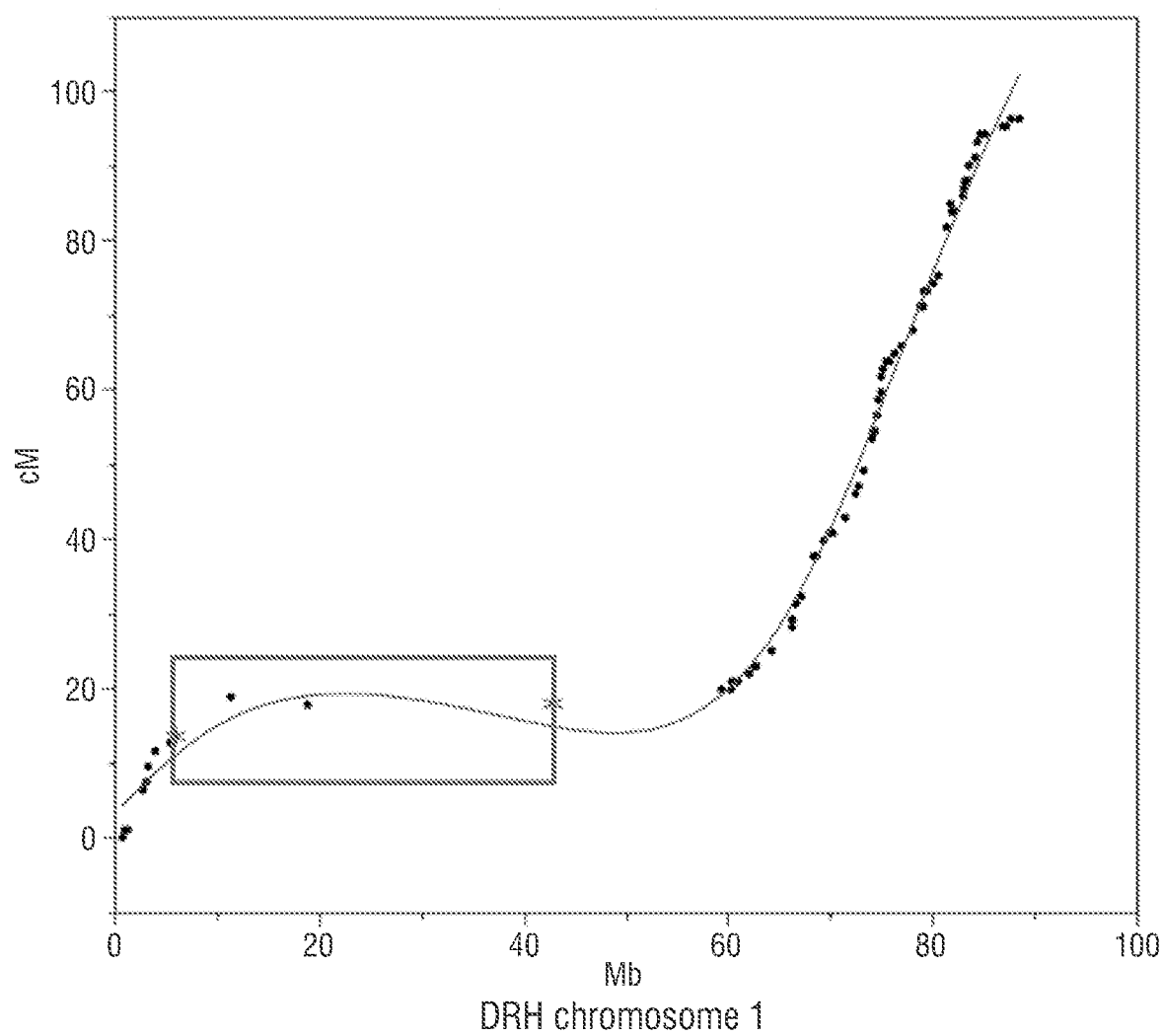
Figure 4A:
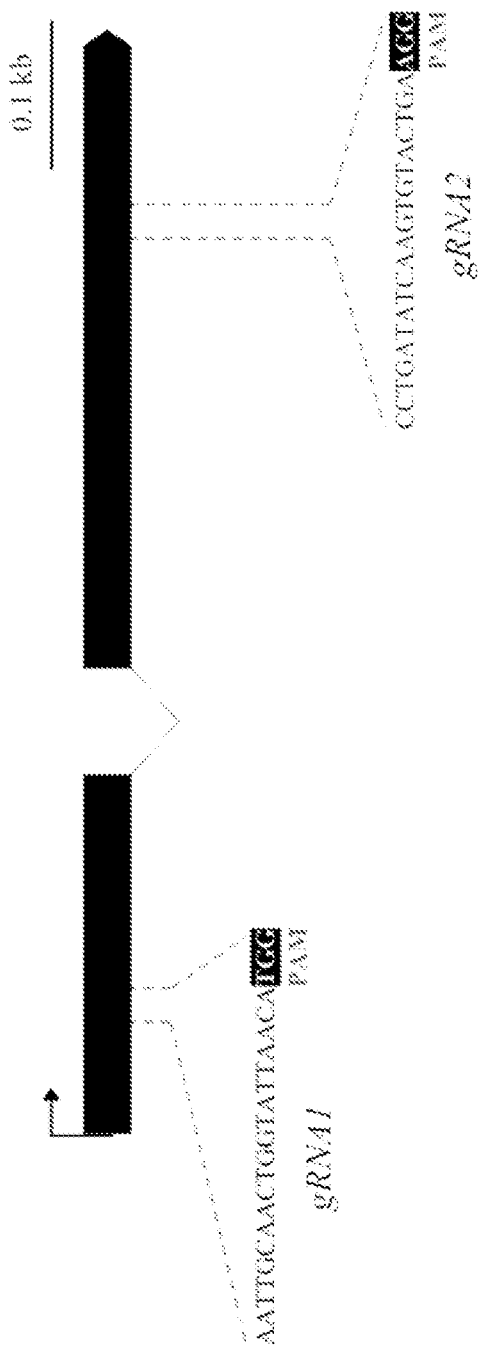
FIG. 4. A. sgRNAs were designed to target each S-RNase exon. B. Transformation events obtained for each diploid line. Red asterisks are showing mono or bi-allelic mutations on DRH-310. C. S-RNAse amplicon sequencing from selected mutant events. SEQ ID NOS 25-33 respectively. D. Self-compatible (left) and self-incompatible (right) transformation events observed in greenhouse.
Figure 4D:
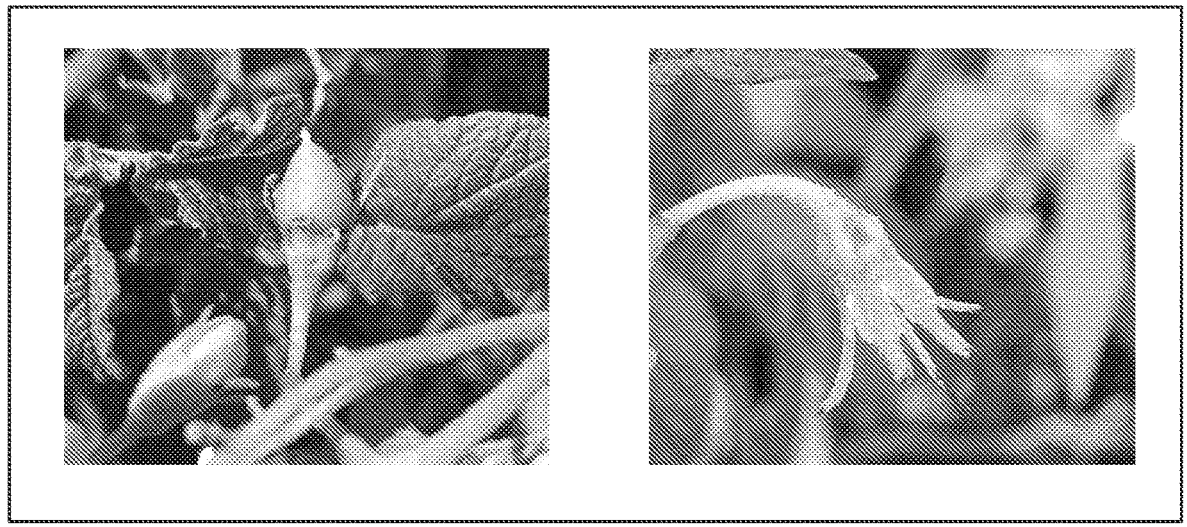

S-RNAse mapping. The S-RNAse gene was mapped to chromosome 1 in a low recombination region near to the centromere (FIG. 3). S-RNase knockout and in-vivo validation. Two sgRNAs were selected to target the S-RNase (FIG. 4A). Transformation events were selected for InDel presence (FIG. 4B, C) and self-pollination assays are being conducted (FIG. 4D). S-RNase alleles were uncovered and targeted for knock-out using CRISPR/Cas9 in self-incompatible diploid lines. A successful S-RNAse target mutagenesis was achieved for both alleles. Self-compatibility will be confirmed by self-pollination and pollen tube growth by aniline blue staining are in progress.

Example 3

Plant material: Two diploid SI lines (DRH-195 and DRH-310) were selected to generate the S-RNase KO lines.

Candidate S-RNase identification and mapping: Reported S-RNase genes were aligned to the *S. tuberosum* (DM). Resulting orthologs were compared with expression data sets and subjected to structural annotation. An RH-allele specific marker was developed and mapped in the previously reported DRH F1 population (Manrique-Carpintero et al., 2015).

S-RNase KO: Guide-RNAs were designed from conserved exonic regions of the S-RNase alleles, assembled into a binary vector carrying the CRISPR/Cas9 cassette and used for *Agrobacterium tumefaciens*-mediated.

Figure 5A:
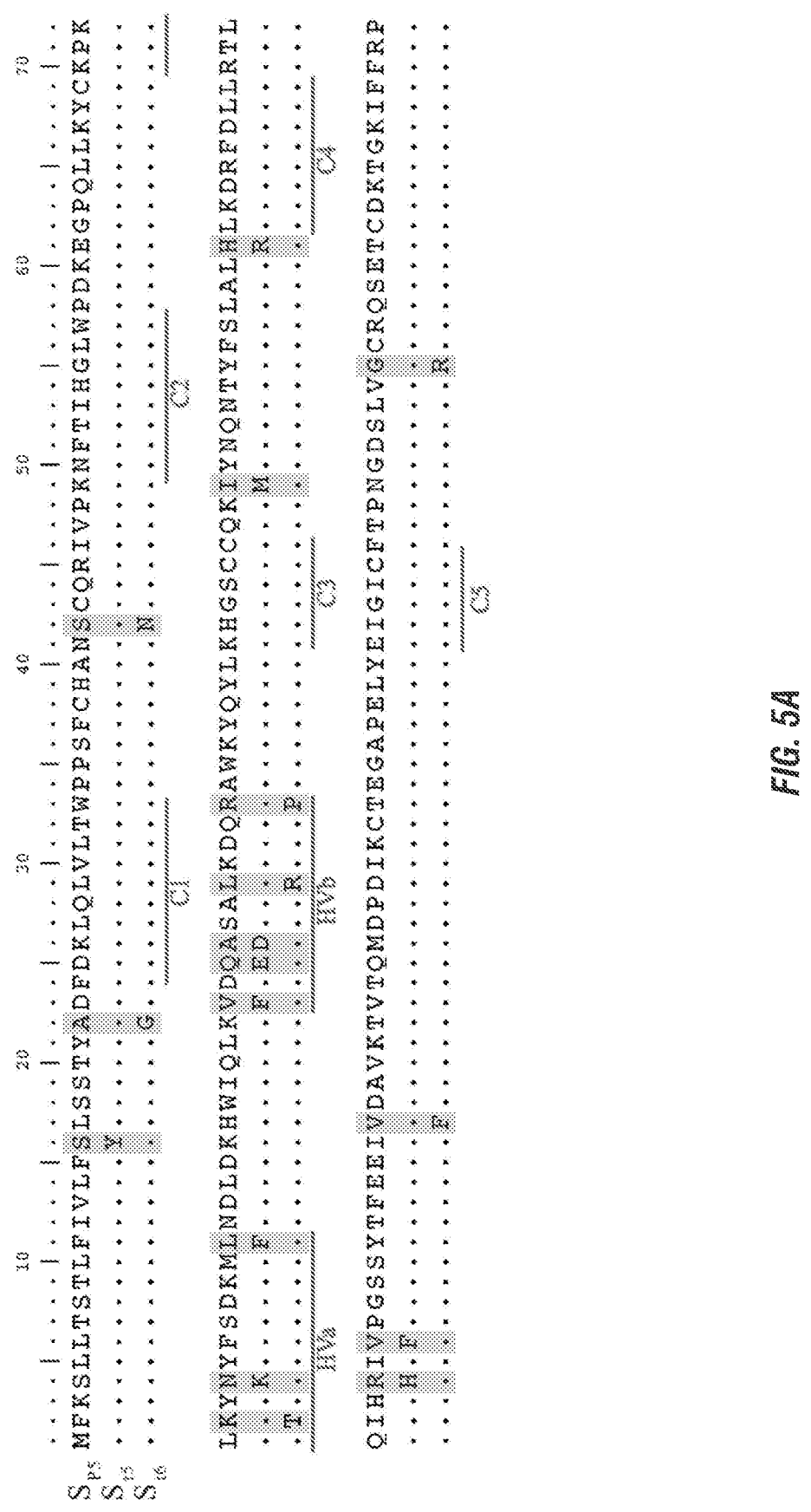
Figure 5B:
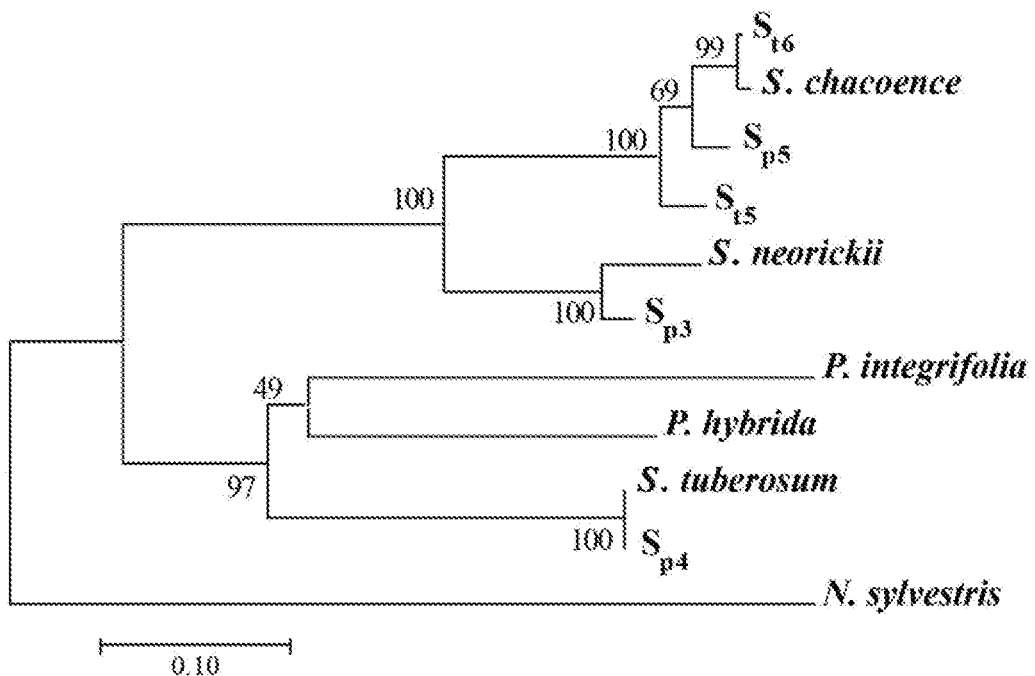
FIG. 5. A. S-RNAse predicted amino-acid sequence alignment of the DM ($S_{p5}$) and RH ($S_{r5}$ and $S_{r6}$) alleles. Underlined regions are the typical five conserved (C1-5) and hypervariable (HVa-b) regions of the S-RNase gene family. B. Phylogenetic tree constructed by Neighbor Joining method using the predicted amino acid sequences of S-RNase alleles. SEQ ID NOS 34-37 respecitvely. C. Detected S-RNase alleles and pairwise amino acid similarity of S-RNase in *Solanum* species D. The S-RNase gene mapped to 16.3 cM on the short arm near the centromeric region of chromosome 1 (red).
Figure 5C:
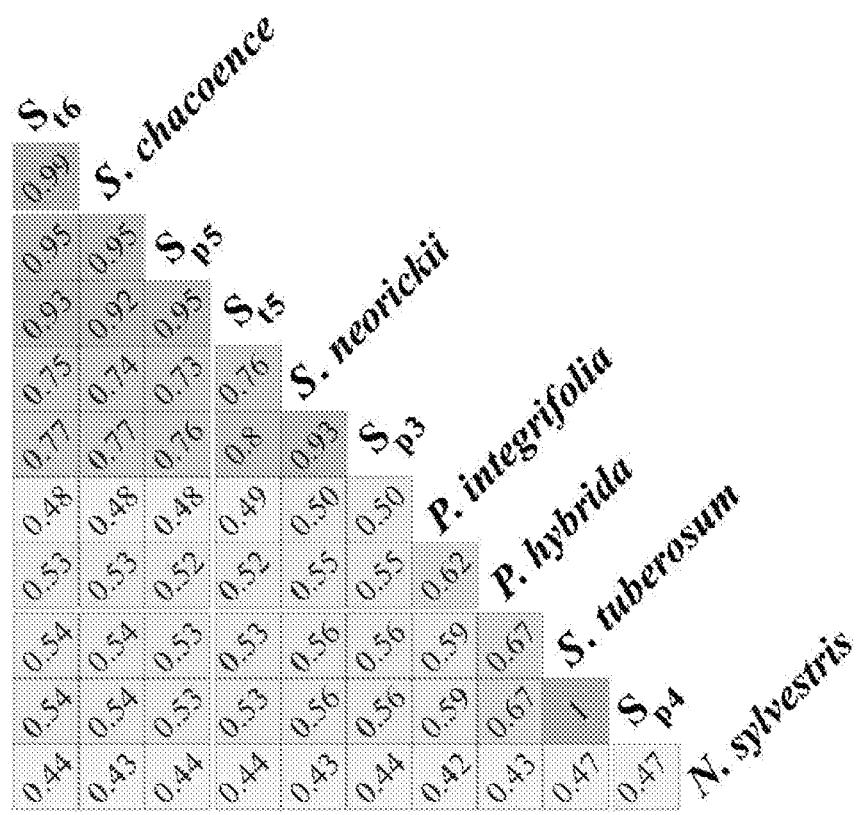
Figure 5D:
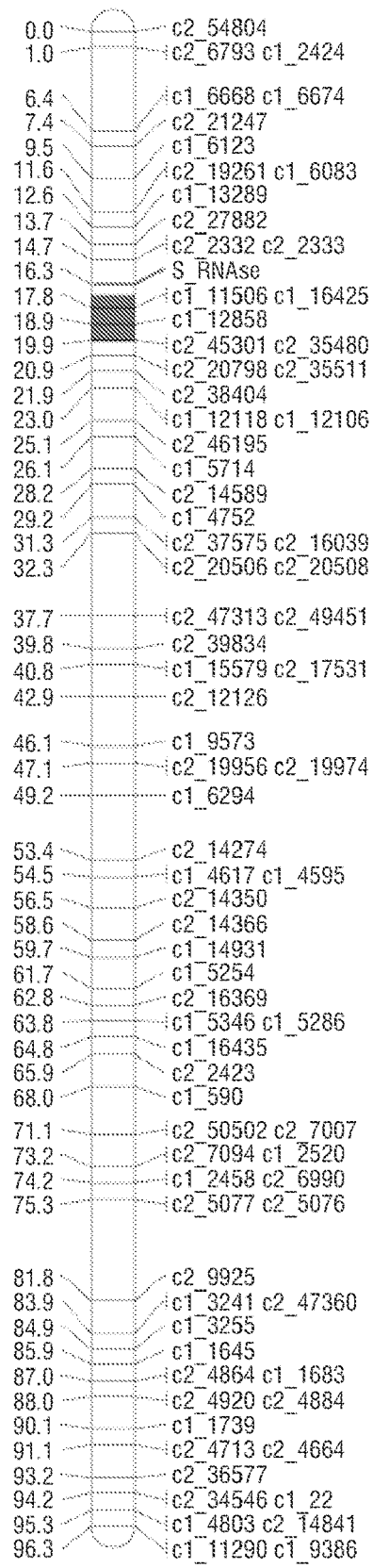

Identification of allelic variants and S-RNase mapping. S-RNase allelic variants were identified in DRH-195 and DRH-310 (FIG. 5A-C). The S-RNase gene was mapped to chromosome 1 in a low recombination region near the centromere (FIG. 5D).

Figures 6A, 6B:
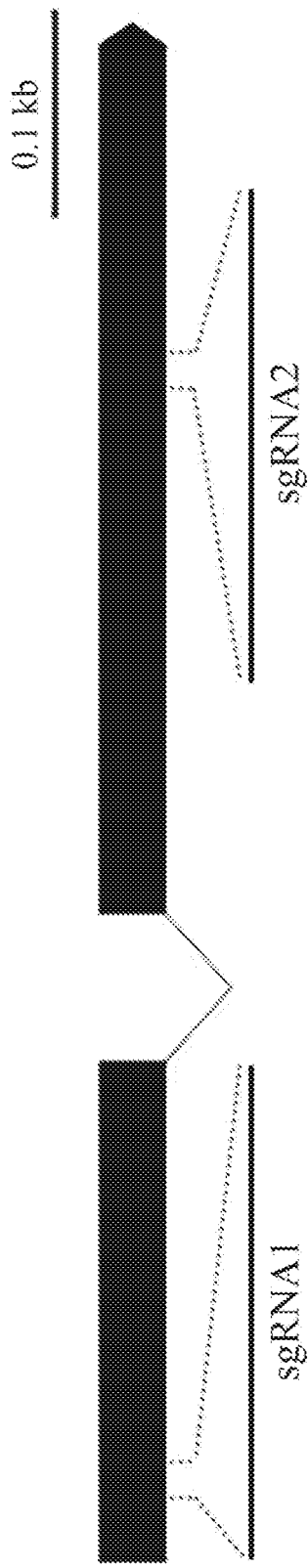
FIG. 6. A. Single-guide RNAs (sgRNAs) designed to target the S-RNase exon1 (sgRNA 1) and exon 2 (sgRNA 2). B. Transformation events selected. Bi-allelic S-RNase KOs for C. DRH-195 and D. DRH-310 T0 lines, detected upon InDel presence. E. Different mutation types detected by amplicon sequencing in selected KOs for DRH-195. Wild-type (WT) S-RNase exhibiting selected sgRNAs (sgRNA1 and sgRNA2) and PAM sequences are shown at the top of each alignment SEQ ID NOS 38-51.

S-RNase KO screening in transformation events. Two sgRNAs were selected to target the S-RNase (FIG. 2A). Transformation events were selected upon InDel presence (FIG. 6B, C-D) and sanger sequenced (FIG. 6E).

Figure 7A:
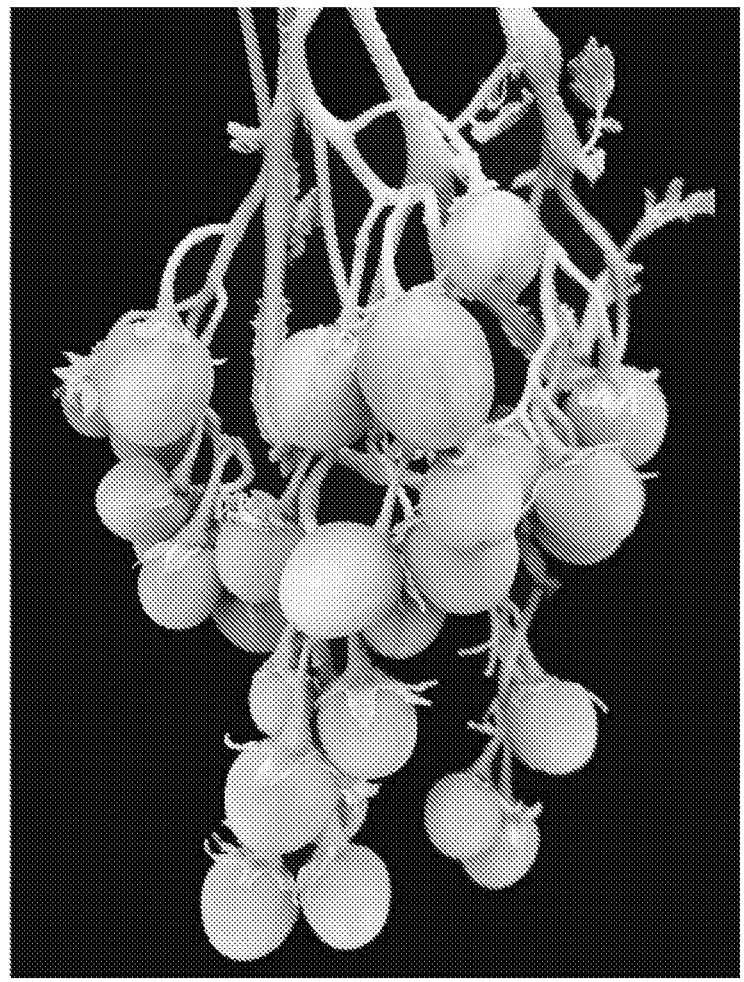
FIG. 7. A. Fruits obtained after five weeks of self-pollination. B. Semi-quantitative reverse transcription PCR (RT-PCR) in DRH-195 and DRH-310 self-pollinated wild-type (WT) and knock-out (KO) T0 lines (DRH-195.158 and DRH-310-21, respectively). S-RNase expression in WT but not in KO lines as compared with the housekeeping gene control (EF1α). C. T1 plants derived from the DRH-195.158 T0 line were screened with the S-RNase primers. C: Negative control. The red box is showing a T1 line segregating out Cas9 while maintaining the S-RNase KO.
Figure 7B:
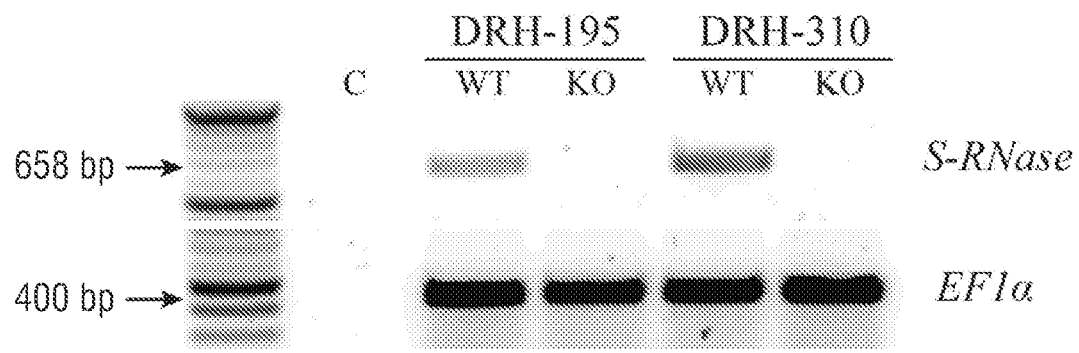
Figure 7C:
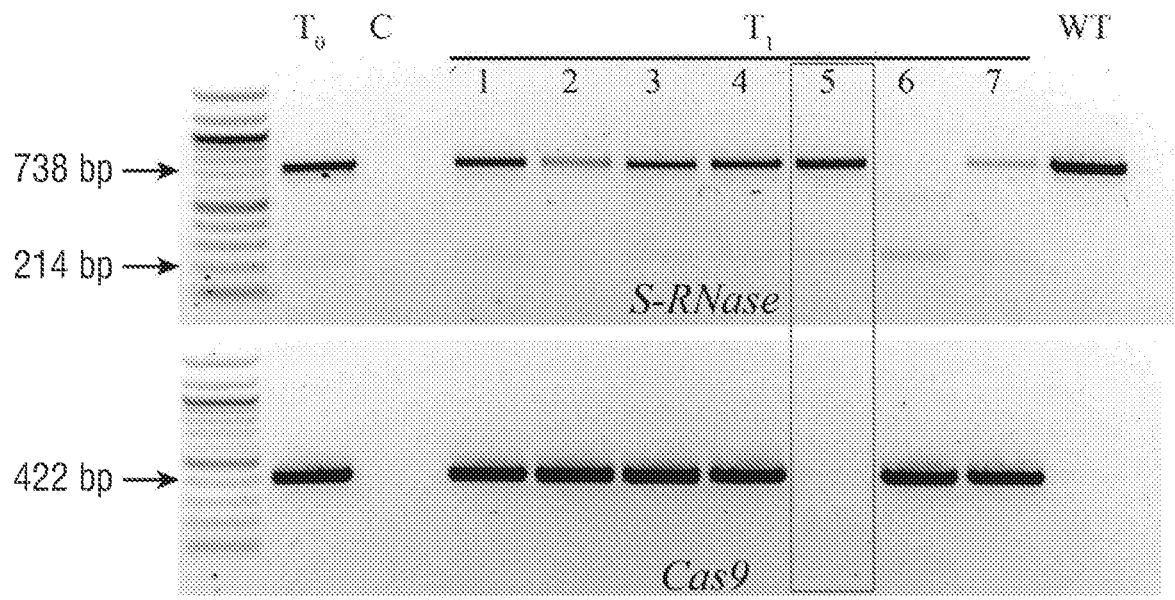

S-RNase KO validation. Self-compatibility was achieved on each selected S-RNase KO line after self-pollination (FIG. 7).

We identified new S-RNase alleles in two SI diploid lines and mapped this gene to chromosome 1. S-RNase KO lines were obtained using a dual sgRNA strategy generating premature stop codons. After self-pollination, fruits were set in selected KO lines and viable $T_1$ seeds were produced. Our results suggest that creating an S-RNase KO can contribute to utilization of self-compatibility as a first step for the generation of commercial diploid cultivars.

Example 3 gRNA sequences:

gRNA1: AATTGCAACTGGTATTAACA (SEQ ID NO: 22)

gRNA2: GGTCTTTGGCCGGATAAGGA (SEQ ID NO: 23)

```
                                                                (SEQ ID NO: 24)
gRNA3: CCTGATATCAAGTGTACTGA

DRH S-RNAse homolog sequence
>DRH S-RNAse
                                                                (SEQ ID NO: 4)
ATGTTTAATCACTGCTTACATCRACTCTCTTCATTGTGCTTTTTTCTCTCTCTTCTACTT

ATGSGGATTTCGACAAATTGCAACTGGTATTAACATGGCCACCATCATTTTGCCACGCCA

ATARTTGTCAACGAATAGTTCCAAAAAAYTTTACGATTCACGGTCTTTGGCCGGATAAGG

AGGGACCACAGCTGTTGAAGTACTGCAAGCCAAAACTTAMMTATAACTATTTCAGTGTAA

RCAGCTTTATTATTTTCTTCAGAACCGGATCCTTTTCTRTTYTGTTTAATTTASTGAAAM

GMTTRTTTTTKAATTTCTTGCAGGATAAGATGCTCAATGAYCTTGACAAACACTGGATTC

AGTTGAAGRTTGATCAAGCTTCTGCTCKAAARGACCAACSAGCATGGAAATATCAATATC

TAAAGCAYGGATCCTGCTGTCAGAAAATCTAYAATCAAAACACGTATTTTAGTTTAGCCT

TGCRCTTAAAAGATAGGTTTGATCTTCTGAGAACTCTCCAAATACATAGAATTGTTCCTG

GATCAAGYTATACATTTGAAGAAATCKTTGACGCCGTCAAAACAGTTACTCAGATGGATC

CTGATATCAAGTGTACTGAAGGAGCACCGGAACTATATGAGATAGGCATATGTTTTACCC

CAAATGGAGATAGTCTAGTTSGTTGTCGTCAAAGTGAAACATGCGACAAAACAGGGAAAA

TATTTTTCCGTCCCTGA

S-RNAse knockout sequences for DRH-195 and DRH-310
>DRH-195.26
                                                                (SEQ ID NO: 5)
ATGTTTAAATCACTGCTTACATCAATATCTAAAGCATGGATCCTGCTGTCAGAAAATCTA

TAATCAAAACACGTATTTTAGTTTAGCCTTGCACTTAAAAGATAGGTTTGATCTTCTGAG

AACTCTCCAAATACATAGAATTGTTCCTGGATCAAGCTATACATTTGAAGAAATCGTTGA

CGCCGTCAAAACAGTTACTCAGATGGATCCTGATATCAAGTACTGAAGGAGCACCGGAAC

TATATGAGATAGGCATATGTTTTACCCCAAATGGAGATAGTCTAGTTCGTTGTCGTCAAA

GTGAAACATGCGACAAAACAGGGAAAATATTTTTCCGTCCCTGA

>DRH-195.118
                                                                (SEQ ID NO: 6)
ATGTTTAAATCACTGCTTACATCGACTCTCTTCATTGTGCTTTTTTCTCTCTCTTCTACT

TATGGGGATTTCGACAAATTGCAACATGGCCACCATCATTTTGCCACGCCAATAATTGTC

AACGAATAGTTCCAAAAAACTTTACGATTCACGGTCTTTGGCCGGATAAGGAGGGACCAC

AGCTGTTGAAGTACTGCAAGCCAAAACTTACCTATAACTATTTCAGTGTAAGCAGCTTTA

TTATTTTCTTCAGAACCGGATCCTTTTCTGTTTTGTTTAATTTACTGAAAAGCTTATTTT

TTAATTTCTTGCAGGATAAGATGCTCAATGATCTTGACAAACACTGGATTCAGTTGAAGA

TTGATCAAGCTTCTGCTCGAAAGGACCAACCAGCATGGAAATATCAATATCTAAAGCACG

GATCCTGCTGTCAGAAAATCTACAATCAAAACACGTATTTTAGTTTAGCCTTGCGCTTAA

AAGATAGGTTTGATCTTCTGAGAACTCTCCAAATACATAGAATTGTTCCTGGATCAAGTT

ATACATTTGAAGAAATCTTTGACGCCGTCAAAACAGGGAAAATATTTTTCCGTCCCTGA

>DRH-195.137.1
                                                                (SEQ ID NO: 7)
ATGTTTAAATCACTGCTTACATCGACTCTCTTCATTTTGCCACGCCAATAATTGTCAACG

AATAGTTCCAAAAAACTTTACGATTCACGGTCTTTGGCCGGATAAGGAGGGACCACAGCT

GTTGAAGTACTGCAAGCCAAAACTTACCTATAACTATTTCAGTGTAAGCAGCTTTATTAT

TTTCTTCAGAACCGGATCCTTTTCTGTTTTGTTTAATTTACTGAAAAGCTTATTTTTTAA

TTTCTTGCAGGATAAGATGCTCAATGATCTTGACAAACACTGGATTCAGTTGAAGATTGA
```

-continued

```
TCAAGCTTCTGCTCGAAAGGACCAACCAGCATGGAAATATCAATATCTAAAGCACGGATC

CTGCTGTCAGAAAATCTACAATCAAAACACGTATTTTAGTTTAGCCTTGCGCTTAAAAGA

TAGGTTTGATCTTCTGAGAACTCTCCAAATACATAGAATTGTTCCTGGATCAAGTTATAC

ATTTGAAGAAATCTTTGACGCCGTCAAAACAGTTACTCAGATGGATCCTGATATCAAGTG

TACTGAAGGAGCACCGGAACTATATGAGATAGGCATATGTTTTACCCCAAATGGAGATAG

TCTAGTTCGTTGTCGTCAAAGTGAAACATGCGACAAAACAGGGAAAATATTTTTCCGTCC

CTGA
```

>DRH-195.158 (SEQ ID NO: 8)

```
ATGTTTAAATCACTGCTTACATCGACTCTCTTCATTGTGCTTTTTTCTCTCTCTTCTACT

TATGGGGATTTCGACAAATTGCAACTGGTATTCTGAAGGAGCACCGGAACTATATGAGAT

AGGCATATGTTTTACCCCAAATGGAGATAGTCTAGTTCGTTGTCGTCAAAGTGAAACATG

CGACAAAACAGGGAAAATATTTTTCCGTCCCTGA
```

>DRH-195.137-2 (SEQ ID NO: 9)

```
ATGTTTAAATCACTGCTTACATCAACTCTCTTCATTGTGCTTTTTTCTCTCTCTTCTACT

TATGCGGATTTCTACTTATGAGATAGGCATATGTTTTACCCCAAATGGAGATAGTCTAGT

TGGTTGTCGTCAAAGTGAAACATGCGACAAAACAGGGAAAATATTTTTCCGTCCCTGA
```

>DRH-195.164 (SEQ ID NO: 10)

```
ATGTTTAAATCACTGCTTACATCGACTCTCTTCATTGTGCTTTTTTCTCTCTCTTCTACT

TATGGGGATTTCGACAAATTGCAACTGGCTGAAGGAGCACCGGAACTATATGAGATAGGC

ATATGTTTTACCCCAAATGGAGATAGTCTAGTTCGTTGTCGTCAAAGTGAAACATGCGAC

AAAACAGGGAAAATATTTTTCCGTCCCTGA
```

>DRH-310.8 (SEQ ID NO: 11)

```
ATGTTTAAATCACTGCTTACATCAACTCTCTTCATTGTGCTTTTTTCTCTCTCTTCTACT

TATGCGGATTTCGACAAATTGCAACTGGTATTCTGAAGGAGCACCGGAACTATATGAGAT

AGGCATATGTTTTACCCCAAATGGAGATAGTCTAGTTGGTTGTCGTCAAAGTGAAACATG

CGACAAAACAGGGAAAATATTTTTCCGTCCCTGA
```

>DRH-195.92 (SEQ ID NO: 12)

```
ATGTTTAAATCACTGCTTACATCAACTCTCTTCATTGTGCTTTTTTCTCTCTCTTCTACT

TATGGGGATTTCGACAAATTGCAACTGGTATTACTGAAGGAGCACCGGAACTATATGAGA

TAGGCATATGTTTTACCCCAAATGGAATAGTCTAGTTCGTTGTCGTCAAAGTGAAACATG

CGACAAAACAGGGAAAATATTTTTCCGTCCCTGA
```

>DRH-195.149.1 (SEQ ID NO: 13)

```
ATGTTTAAATCACTGCTTACATCAACTCTCTTCATTGTGCTTTTTTCTCTCTCTTCTACT

TATGCGGATTTCGACAAATTGCAACTGGTATTTTACGATTCACGGTCTTTGGCCGGATAA

GGAGGGACCACAGCTGTTGAAGTACTGCAAGCCAAAACTTAAATATAACTATTTCAGTGT

AAACAGCTTTATTATTTTCTTCAGAACCGGATCCTTTTCTATTCTGTTTAATTTAGTGAA

ACGATTGTTTTTGAATTTCTTGCAGGATAAGATGCTCAATGACCTTGACAAACACTGGAT

TCAGTTGAAGGTTGATCAAGCTTCTGCTCTAAAAGACCAACGAGCATGGAAATATCAATA

TCTAAAGCATGGATCCTGCTGTCAGAAAATCTATAATCAAAACACGTATTTTAGTTTAGC

CTTGCACTTAAAAGATAGGTTTGATCTTCTGAGAACTCTCCAAATACATAGAATTGTTCC
```

```
TGGATCAAGCTATACATTTGAAGAAATCGTTGACGCCGTCAAAACAGTTACCCAAATGGA

GATAGTCTAGTTGGTTGTCGTCAAAGTGAAACATGCGACAAAACAGGGAAAATATTTTC

CGTCCCTGA

>DRH-195.149.2                                                (SEQ ID NO: 14)

ATGTTTAAATCACTGCTTACATCAACTCTCTTCATTGTGCTTTTTTCTCTCTCTTCTACT

TATGCGGATTTCGACAAATTGCAACTGGTATTTTACGATTCACGGTCTTTGGCCGGATAA

GGAGGGACCACAGCTGTTGAAGTACTGCAAGCCAAAACTTAAATATAACTATTTCAGTGT

AAACAGCTTTATTATTTTCTTCAGAACCGGATCCTTTTCTATTCTGTTTAATTTAGTGAA

ACGATTGTTTTGAATTTCTTGCAGGATAAGATGCTCAATGACCTTGACAAACACTGGAT

TCAGTTGAAGGTTGATCAAGCTTCTGCTCTAAAAGACCAACGAGCATGGAAATATCAATA

TCTAAAGCATGGATCCTGCTGTCAGAAAATCTATAATCAAAACACGTATTTTAGTTTAGC

CTTGCACTTAAAAGATAGGTTTGATCTTCTGAGAACTCTCCAAATACATAGAATTGTTCC

TGGATCAAGCTATACATTTGAAGAAATCGTTGACGCCGTCAAAACAGTTACCCAAATGGA

GATAGTCTAGTTGGTTGTCGTCAAAGTGAAACATGCGACAAAACAGGGAAAATATTTTC

CGTCCCTGA

>DRH-195.105                                                  (SEQ ID NO: 15)

ATGTTTAAATCACTGCTTACATCAACTCTCTTCATTGTGCTTTTTTCTCTCTCTTCTACT

TATGCGGATTTCGACAAATTGCAACTGGTCTGAAGGAGCACCGGAACTATATGAGATAGG

CATATGTTTTACCCCAAATGGAGATAGTCTAGTTGGTTGTCGTCAAAGTGAAACATGCGA

CAAAACAGGGAAAATATTTTTCCGTCCCTGA

>DRH-310.33                                                   (SEQ ID NO: 16)

ATGTTTAAATCACTGCTTACATCAACTCTCTTCATTGTGCTTTTTTCTCTCTCTTCTACT

TATGCGGATTTCGACAAATTGCAACTGGTATTTTACGATTCACGGTCTTTGGCCGGATAA

GGAGGGACCACAGCTGTTGAAGTACTGCAAGCCAAAACTTAAATATAACTATTTCAGTGT

AAACAGCTTTATTATTTTCTTCAGAACCGGATCCTTTTCTATTCTGTTTAATTTAGTGAA

ACGATTGTTTTGAATTTCTTGCAGGATAAGATGCTCAATGACCTTGACAAACACTGGAT

TCAGTTGAAGGTTGATCAAGCTTCTGCTCTAAAAGACCAACGAGCATGGAAATATCAATA

TCTAAAGCATGGATCCTGCTGTCAGAAAATCTATAATCAAAACACGTATTTTAGTTTAGC

CTTGCACTTAAAAGATAGGTTTGATCTTCTGAGAACTCTCCAAATACATAGAATTGTTCC

TGGATCAAGCTATACATTTGAAGAAATCGTTGACGCCGTCAAAACAGTTACCCAAATGGA

GATAGTCTAGTTGGTTGTCGTCAAAGTGAAACATGCGACAAAACAGGGAAAATATTTTC

CGTCCCTGA

>DRH-195.38                                                   (SEQ ID NO: 17)

ATGTTTAAATCACTGCTTACATCAACTCTCTTCATTGTGCTTTTTTCTCTCTCTTCTACT

TATGCGGATTTCGACAAATTGCAACTGGTATTAAACATGGCCACCATCATTTTGCCACGC

CAATAGTTGTCAACGAATAGTTCCAAAAAATTTTACGATTCACGGTCTTTGGCCGGATAA

GGAGGGACCACAGCTGTTGAAGTACTGCAAGCCAAAACTTAAATATAACTATTTCAGTGT

AAACAGCTTTATTATTTTCTTCAGAACCGGATCCTTTTCTATTCTGTTTAATTTAGTGAA

ACGATTGTTTTGAATTTCTTGCAGGATAAGATGCTCAATGACCTTGACAAACACTGGAT

TCAGTTGAAGGTTGATCAAGCTTCTGCTCTAAAAGACCAACGAGCATGGAAATATCAATA

TCTAAAGCATGGATCCTGCTGTCAGAAAATCTATAATCAAAACACGTATTTTAGTTTAGC
```

-continued

CTTGCACTTAAAAGATAGGTTTGATCTTCTGAGAACTCTCCAAATACATAGAATTGTTCC

TGGATAATAACTCACACTTGCCACTGCTTCATCTATCGTCAAAGTGAAACATGCGACAAA

ACAGGGAAAATATTTTTCCGTCCCTGA

>DRH-195.55 (SEQ ID NO: 18)

ATGTTTAAATCACTGCTTACATCAACTCTCTTCATTGTGCTTTTTTCTCTCTCTTCTACT

TATGCGGATTTCGACAAATTGCAACTGGTATTACTGAAGGAGCACCGGAACTATATGAGA

TAGGCATATGTTTTACCCCAAATGGAGATAGTCTAGTTGGTTGTCGTCAAAGTGAAACAT

GCGACAAAACAGGGAAAATATTTTTCCGTCCCTGA

>DRH-195.160 (SEQ ID NO: 19)

ATGTTTAAATCACTGCTTACATCAACTCTCTTCATTGTGCTTTTTTCTCTCTCTTCTACT

TATGCGGATTTCGACAAATTGCAACTGGCCACCATCATTTTGCCACGCCAATAGTTGTCA

ACGAATAGTTCCAAAAAATTTTACGATTCACGGTCTTTGGCCGGATAAGGAGGGACCACA

GCTGTTGAAGTACTGCAAGCCAAAACTTAAATATAACTATTTCAGTGTAAACAGCTTTAT

TATTTTCTTCAGAACCGGATCCTTTTCTATTCTGTTTAATTTAGTGAAACGATTGTTTTT

GAATTTCTTGCAGGATAAGATGCTCAATGACCTTGACAAACACTGGATTCAGTTGAAGGT

TGATCAAGCTTCTGCTCTAAAAGACCAACGAGCATGGAAATATCAATATCTAAAGCATGG

ATCCTGCTGTCAGAAAATCTATAATCAAAACACGTATTTTAGTTTAGCCTTGCACTTAAA

AGATAGGTTTGATCTTCTGAGAACTCTCCAAATACATAGAATTGTTCCTGAACATCACCA

AGCACCTTTGGAGATAGTCTAGTTGGTTGTCGTCAAAGTGAAACATGCGACAAAACAGGG

AAAATATTTTTCCGTCCCTGA

>DRH-195.166 (SEQ ID NO: 20)

ATGTTTAAATCACTGCTTACATCAACTCTCTTCATTGTGCTTTTTTCTCTCTCTTCTACT

TATGCGGATTTCGACAAATTGCAACTGGTATTACCCATGGCCACCATCATTTTGCCACGC

CAATAGTTGTCAACGAATAGTTCCAAAAAATTTTACGATTCACGGTCTTTGGCCGGATAA

GGAGGGACCACAGCTGTTGAAGTACTGCAAGCCAAAACTTAAATATAACTATTTCAGCGT

AAACAGCTTTATTATTTTCTTCAGAACCGGATCCTTTTCTATTCTGTTTAATTTAGTGAA

AAAATTGCTATAGAATCTATTGAAATGTTTATCTGCAATGACTATGAATGC

>DRH-310.21 (SEQ ID NO: 21)

ATGTTTAAATCACTGCTTACATCAACTCTCTTCATTGTGCTTTTTTCTCTCTCTTCTACT

TATGCGGATTTCGACAAATTGCAACTGGACATGGCCACCATCATTTTGCCACGCCAATAG

TTGTCAACGAATAGTTCCAAAAAATTTTACGATTCACGGTCTTTGGCCGGATAAGGAGGG

ACCACAGCTGTTGAAGTACTGCAAGCCAAAACTTAAATATAACTATTTCAGTGTAAACAG

CTTTATTATTTTCTTCAGAACCGGATCCTTTTCTATTCTGTTTAATTTAGTGAAACGATT

GTTTTTGAATTTCTTGCAGGATAAGATGCTCAATGACCTTGACAAACACTGGATTCAGTT

GAAGGTTGATCAAGCTTCTGCTCTAAAAGACCAACGAGCATGGAAATATCAATATCTAAA

GCATGGATCCTGCTGTCAGAAAATCTATAATCAAAACACGTATTTTAGTTTAGCCTTGCA

CTTAAAAGATAGGTTTGATCTTCTGAGAACTCTCCAAATACATAGAATTGTTCCTGGATC

AAGCTATACATTTGAAACATGCGACAAACAGGGAAAATATTTTTCCGTCCCTGA

FIG. 4C
WT
(SEQ ID NO: 25)

GATTTCGACAAATTGCAACTGGTATTAACATGGCCACCATCAT//CAGATGGATCCTGATATCA

-continued

AGTGTACTGAAGGAGCACCGGAA

FIG. 4C
195-104.1 (SEQ ID NO: 26)

GATTTCGACAAATTGCAACTGGTATTNNNNNNNNNNNNNNNNNNNN//NNNNNNNNNNNNNNNNNNN

NNNNNNCTGAAGGAGCACCGGAA

FIG. 4C
195-104.2 (SEQ ID NO: 27)

GATTTCGACAAATTGCAACTGGT//CTGAAGGAGCACCGGAA

FIG. 4C
195-105.1 (SEQ ID NO: 28)

GATTTCGACAAATTGCAACTGGTACATGGCCACCATCAT//CAGATGGATCCTGATATCAAGTG

TGAAGGAGCACCGGAA

FIG. 4C
195-105.2 (SEQ ID NO: 29)

GATTTCGACAAATTGCAACTGGT//GAAGGAGCACCGGAA

FIG. 4C
195-137.1 (SEQ ID NO: 30)

//CAGATGGATCCTGATATCAAGTGTACTGAAGGAGCACCGGAA

FIG. 4C
310-8 (SEQ ID NO: 31)

GATTTCGACAAATTGCAACTGGTATT//CTGAAGGAGCACCGGAA

FIG. 4C
310-33 (SEQ ID NO: 32)

GATTTCGACAAATTGCAACTGGTATT//

FIG. 4C
310-47 (SEQ ID NO: 33)

GATTTC//CTGAAGGAGCACCGGAA

S-RNaseDM FIG. 5B (SEQ ID NO: 34)

MFKSLLTSTLFIVLFSLSSTYADFDKLQLVLTWPPSFCHANSCQRIVPKNFTIHGLWPDK

EGPQLLKYCKPKLKYNYFSDKMLNDLDKHWIQLKVDQASALKDQRAWKYQYLKHGSCCQK

IYNQNTYFSLALHLKDRFDLLRTLQIHRIVPGSSYTFEEIVDAVKTVTQMDPDIKCTEGA

PELYEIGICFTPNGDSLVGCRQSETCDKTGKIFFRP

S-RNaseM6 FIG. 5B (SEQ ID NO: 35)

MVKPQLTSALFIVLFALSPAYGDFDSLQLVLTWPASFCHVNDCVRIAPKNFTIHGLWPDK

EGTVLQNCKPKPKYVNFKDKMFNDLDKHWIQLKFDEDYGEKEQPLWLYQYFKHGSCCQK

MYNQNTYFSLALRLKDRFDLLRTLQIHHIFPGSSYTFKKIFDAVKTATQMDPDLKCTKGV

PELYEIGICFTPNADALIPCRQX

S1-RNAseRH FIG. 5B (SEQ ID NO: 36)

MFKSLLTSTLFIVLFYLSSTYADFDKLQLVLTWPPSFCHANSCQRIVPKNFTIHGLWPDK

EGPQLLKYCKPKLKYKYFSDKMFNDLDKHWIQLKFDEDSALKDQRAWKYQYLKHGSCCQK

MYNQNTYFSLALRLKDRFDLLRTLQIHHIFPGSSYTFEEIVDAVKTVTQMDPDIKCTEGA

PELYEIGICFTPNGDSLVGCRQSETCDKTGKIFFRP

S2-RNAseRH FIG. 5B (SEQ ID NO: 37)

MFKSLLTSTLFIVLFYLSSTYGDFDKLQLVLTWPPSFCHANNCQRIVPKNFTIHGLWPDK

EGPQLLKYCKPKLTYNYFSDKMLNDLDKHWIQLKIDQASARKDQPAWKYQYLKHGSCCQK

IYNQNTYFSLALRLKDRFDLLRTLQIHRIVPGSSYTFEEIFDAVKTVTQMDPDIKCTEGA

PELYEIGICFTPNGDSLVRCRQSETCDKTGKIFFRP

WT FIG. 6E (SEQ ID NO: 38)

ATTTCGACAAATTGCAACTGGTATTAACATGGCCACCATCA//AGATGGATCCTGATATCAAGTGT

ACTGAAGGAGCACCGGA 195-104DM FIG. 6E (SEQ ID NO: 39)

ATTTCGACAAATTGCAACTGGT//CTGAAGGAGCACCGGA 195-104RH FIG. 6E (SEQ ID NO: 40)

ATTTCGACAAATTGCAACTGGTATTAGATATCAGGATCCAT//TGGCAAAATGATGGTGGCCATGT

TCTGAAGGAGCACCGGA 195-105DM FIG. 6E (SEQ ID NO: 41)

ATTTCGACAAATTGCAACTGGT//CTGAAGGAGCACCGGA 195-105RH FIG. 6E (SEQ ID NO: 42)

ATTTCGACAAATTGCAACTGGTACATGGCCACCATCA//AGATGGATCCTGATATCAAGTGTGAAG

GAGCACCGGA 195-128DM FIG. 6E (SEQ ID NO: 43)

ATTTCGACAAATTGCAACTGGTATTAAACATGGCCACCATC//AGATGGATCCTGATATCAAGTGT

ACTGAAGGAGCACCGGA 195-128RH FIG. 6E (SEQ ID NO: 44)

ATTTCGACAAATTGCAACTGG//

195-137RH FIG. 6E (SEQ ID NO: 45)

TC//AGATGGATCCTGATATCAAGTGTACTGAAGGAGCACCGGA 195-142DM FIG. 6E (SEQ ID NO: 46)

ATTTCGACAAATTGCAACTGGTACATGGCCACCATCA//

195-142RH FIG. 6E (SEQ ID NO: 47)

ATTTCGACAAATTGCAACTGGTACATGGCCACCATCA//AGATGGATCCTGATATCAAGTGTGAAG

GAGCACCGGA 195-158DM FIG. 6E (SEQ ID NO: 48)

ATTTCGACAAATTGCAACTGGTATTACATGGCCACCATCA//AGATGGATCCTGATATCAAGTGTC

TGAAGGAGCACCGGA 195-158RH FIG. 6E (SEQ ID NO: 49)

ATTTCGACAAATTGCAACTGGTATTA//CTGAAGGAGCACCGGA 195-160DM FIG. 6E (SEQ ID NO: 50)

ATTTCGACAAATTGCAACTGGCCACCATCA//

195-160RH FIG. 6E (SEQ ID NO: 51)

ATTTCGACAAATTGCAACTGGCCACCATCA//AGATGGATCCTGATATCAAGTCTGAAGGAGCACC

GGA

>S_RNAse_195_RH_allele (+)

(SEQ ID NO: 1)

ATGTTTAAATCACTGCTTACATCGACTCTCTTCATTGTGCTTTTTTCTCTCTCTTCTACT

TATGGGGATTTCGACAAATTGCAACTGGTATTAACATGGCCACCATCATTTTGCCACGCC

```
AATAATTGTCAACCAATAGTTCCAAAAAACTTTACGATTCACGGTCTTTGGCCGGATAAG

GAGGGACCACAGCTGTTGAAGTACTGCAAGCCAAAACTTACCTATAACTATTTCAGTGTA

AGCAGCTTTATTATTTTCTTCAGAACCGGATCCTTTTCTGTTTTGTTTAATTTACTGAAA

AGCTTATTTTTTAATTTCTTGCAGGATAAGATGCTCAATGATCTTGACAAACACTGGATT

CAGTTGAAGATTGATCAAGCTTCTGCTCGAAAGGACCAACCAGCATGGAAATATCAATAT

CTAAAGCACGGATCCTGCTGTCAGAAAATCTACAATCAAAACACGTATTTTAGTTTAGCC

TTGCGCTTAAAAGATAGGTTTGATCTTCTGAGAACTCTCCAAATACATAGAATTGTTCCT

GGATCAAGTTATACATTTGAAGAAATCTTTGACGCCGTCAAAACAGTTACTCAGATGGAT

CCTGATATCAAGTGTACTGAAGGAGCACCGGAACTATATGAGATAGGCATATGTTTTACC

CCAAATGGAGATAGTCTAGTTCGTTGTCGTCAAAGTGAAACATGCGACAAAACAGGGAAA

ATATTTTTCCGTCCCTGA
```

SEQ ID NO: 52

```
MFKSLLTSTLFIVLFSLSSTYGDFDKLQLVLTWPPSFCHANNCQRIVPKNFTIHGLWPDKEGPQLLKYCKPK

LTYNYFSVSSFIIFFRTGSFSVLFNLLKSLFFNFLQDKMLNDLDKHWIQLKIDQASARKDQPAWKYQYLKHG

SCCQKIYNQNTYFSLALRLKDRFDLLRTLQIHRIVPGSSYTFEEIFDAVKTVTQMDPDIKCTEGAPELYEIG

ICFTPNGDSLVRCRQSETCDKTGKIFFRP
```

>S_RNAse_310_RH_allele (+)

(SEQ ID NO: 2)

```
ATGTTTAAATCACTGCTTACATCAACTCTCTTCATTGTGCTTTTTTATCTCTCTTCTACT

TATGCGGATTTCGACAAATTGCAACTGGTATTAACATGGCCACCATCATTTTGCCACGCC

AATAGTTGTCAACGAATAGTTCCAAAAAATTTTACGATTCACGGTCTTTGGCCGGATAAG

GAGGGACCACAGCTGTTGAAGTACTGCAAGCCAAAACTTAAATATAAATATTTCAGTGTA

AACAGCTTTATTATTTTCTTCAGAACCGGATCCTTTTCTATTCTGTTTAATTTAGTGAAA

CGATTGTTTTTGAATTTCTTGCAGGATAAGATGTTCAACGATCTTGACAAACACTGGATT

CAGTTGAAGTTTGATGAAGATTCTGCTCTAAAAGACCAACGAGCATGGAAATATCAATAT

TTAAAGCATGGATCTTGTTGTCAGAAAATGTACAACCAAAACACGTATTTTAGTCTAGCC

TTGCGCTTAAAAGACAGGTTTGATCTTCTGAGAACTCTCCAAATACATCATATTTTCCT

GGATCAAGTTATACATTTGAAGAAATCGTTGACGCCGTCAAAACAGTTACTCAGATGGAT

CCTGATATCAAGTGTACTGAAGGAGCACCGGAACTATATGAGATAGGCATATGTTTTACC

CCAAATGGAGATAGTCTAGTTGGTTGTCGTCAAAGTGAAACATGCGACAAAACAGGGAAA

ATATTTTTCCGTCCCTGA
```

SEQ ID NO: 53

```
MFKSLLTSTLFIVLFYLSSTYADFDKLQLVLTWPPSFCHANSCQRIVPKNFTIHGLWPDKEGPQLLK

YCKPKLKYKYFSVNSFIIFFRTGSFSILFNLVKRLFLNFLQDKMFNDLDKHWIQLKFDEDSALKDQR

AWKYQYLKHGSCCQKMYNQNTYFSLALRLKDRFDLLRTLQIHHIFPGSSYTFEEIVDAVKTVTQM

DPDIKCTEGAPELYEIGICFTPNGDSLVGCRQSETCDKTGKIFFRP
```

>S_RNAse_DM_aalele (+)

(SEQ ID NO: 3)

```
ATGTTTAAATCACTGCTTACATCAACTCTCTTCATTGTGCTTTTTCTCTCTTCTACTTATGCGGATTTCGACAAATT

GCAACTGGTATTAACATGGCCACCATCATTTTGCCACGCCAATAGTTGTCAACGAATAGTTCCAAAAAATTTTACGATTC

ACGGTCTTTGGCCGGATAAGGAGGGACCACAGCTGTTGAAGTACTGCAAGCCAAAACTTAAATATAACTATTTCAGTGTA

AACAGCTTTATTATTTTCTTCAGAACCGGATCCTTTTCTATTCTGTTTAATTTAGTGAAACGATTGTTTTTGAATTTCTT

GCAGGATAAGATGCTCAATGACCTTGACAAACACTGGATTCAGTTGAAGGTTGATCAAGCTTCTGCTCTAAAAGACCAAC
```

-continued

```
GAGCATGGAAATATCAATATCTAAAGCATGGATCCTGCTGTCAGAAAATCTATAATCAAAACACGTATTTTAGTTTAGCC

TTGCACTTAAAAGATAGGTTTGATCTTCTGAGAACTCTCCAAATACATAGAATTGTTCCTGGATCAAGCTATACATTTGA

AGAAATCGTTGACGCCGTCAAAACAGTTACTCAGATGGATCCTGATATCAAGTGTACTGAAGGAGCACCGGAACTATATG

AGATAGGCATATGTTTTACCCCAAATGGAGATAGTCTAGTTGGTTGTCGTCAAAGTGAAACATGCGACAAAACAGGGAAA

ATATTTTTCCGTCCCTGA
```

SEQ ID NO: 54

```
MFKSLLTSTLFIVLFSLSSTYADFDKLQLVLTWPPSFCHANSCQRIVPKNFTIHGLWPDKEGPQLLKYCKPK

LKYNYFSVNSFIIFFRTGSFSILFNLVKRLFLNFLQDKMLNDLDKHWIQLKVDQASALKDQRAWKYQYLKHG

SCCQKIYNQNTYFSLALHLKDRFDLLRTLQIHRIVPGSSYTFEEIVDAVKTVTQMDPDIKCTEGAPELYEIG

ICFTPNGDSLVGCRQSETCDKTGKIFFRP
```

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention as described in the appended claims.

The invention claimed is:

1. A method for reducing self-incompatibility in a diploid potato plant comprising: introducing a mutation into an endogenous S RNAse gene that decreases the expression and/or activity of the endogenous S RNAse gene and/or protein in said plant or plant part, plant organ or plant cell of said plant, wherein the endogenous S RNAse gene comprises a nucleotide sequence having at least 99% sequence identity to SEQ ID NO: 1 or at least 95% sequence identity to SEQ ID NO: 2 or 3.

2. The method according to claim 1, wherein the mutation is a knock-out allele of the endogenous S RNAse gene.

3. A method for producing a self-compatible diploid potato plant comprising:
   introducing a mutation into the plant that reduces or eliminates the activity of an endogenous S RNAse gene, wherein the endogenous S RNAse gene comprises the nucleotide sequence set forth in SEQ ID NO: 1, 2, or 3.

4. The method of claim 1, wherein the mutation is introduced by genome editing.

5. The method of claim 4, wherein said genome editing includes one or more of CRISPR/Cas system, Cre/Lox system, TALEN system, zinc finger nuclease (ZNF) system and homologous recombination.

6. The method of claim 1, wherein introducing the mutation comprises providing a Cas9 polypeptide and a guide RNA to at least one cell of the plant.

7. The method of claim 6, wherein the guide RNA comprises the nucleotide sequence set forth in SEQ ID NO: 22, 23, or 24.

8. The method of claim 1, wherein the mutation comprises an insertion or a deletion of one or more nucleotides in the endogenous S RNAse gene.

9. The method of claim 1, wherein the mutation in the endogenous S RNAse gene comprises the nucleotide sequence set forth in SEQ ID NO: 5, 6, 7, 8, 9, 10, 11, 12, 13, 14, 15, 16, 17, 18, 19, 20, or 21.

10. The method of claim 1, wherein the mutation in the endogenous S RNAse gene comprises the nucleotide sequence set forth in SEQ ID NO: 8.

11. The method of claim 1, wherein the diploid potato plant is a *Solanum tuberosum* plant.

* * * * *